United States Patent
Lobo et al.

(10) Patent No.: US 11,717,321 B2
(45) Date of Patent: Aug. 8, 2023

(54) ACCESS ASSEMBLY WITH RETENTION MECHANISM

(71) Applicant: Covidien LP, Mansfield, MA (US)

(72) Inventors: Astley C. Lobo, West Haven, CT (US); Kevin Desjardin, Prospect, CT (US); Douglas M. Pattison, East Hartford, CT (US); Christopher A. Tokarz, Torrington, CT (US); Oksana Buyda, East Haven, CT (US); Amanda M. Adinolfi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 455 days.

(21) Appl. No.: 16/857,476

(22) Filed: Apr. 24, 2020

(65) Prior Publication Data

US 2021/0330352 A1    Oct. 28, 2021

(51) Int. Cl.
*A61B 17/34* (2006.01)

(52) U.S. Cl.
CPC .... *A61B 17/3423* (2013.01); *A61B 2017/347* (2013.01); *A61B 2017/3486* (2013.01); *A61B 2017/3492* (2013.01)

(58) Field of Classification Search
CPC ............ A61B 17/3415; A61B 17/3421; A61B 17/3423; A61B 2017/3407; A61B 2017/3441; A61B 2017/347; A61B 2017/3486; A61B 2017/3492; A61M 16/0497; A61M 25/02; A61M 2025/024;
(Continued)

(56) References Cited

U.S. PATENT DOCUMENTS

| 3,402,710 | A | 9/1968 | Paleschuck |
| 3,495,586 | A | 2/1970 | Regenbogen |

(Continued)

FOREIGN PATENT DOCUMENTS

| CA | 2702419 A1 | 11/2010 |
| CN | 202313634 U | 7/2012 |

(Continued)

OTHER PUBLICATIONS

European Search Report dated Sep. 24, 2021, corresponding to counterpart European Application No. 21170137.0; 8 pages.
(Continued)

*Primary Examiner* — Diane D Yabut
(74) *Attorney, Agent, or Firm* — Carter, DeLuca & Farrell LLP

(57) ABSTRACT

A retention mechanism for a surgical access assembly is provided. The retention mechanism includes a planar base having first and second extensions each with a free end, a first locking member disposed on the free end of the first extension, and a second locking member disposed on the free end of the second extension. The first locking member includes a U-shaped body having a first set of opposed, inwardly facing teeth. The second locking member includes a U-shaped body having a first set of opposed, outwardly facing teeth configured engage the first set of opposed, inwardly facing teeth when the retention mechanism is in a locked condition. The first set of opposed, inwardly facing teeth and the first set of opposed, outwardly facing teeth are configured to be spaced apart from each other when the retention mechanism is in an unlocked condition.

20 Claims, 13 Drawing Sheets

(58) Field of Classification Search
CPC .......... F16G 11/04; F16K 7/065; F16K 7/066; F16L 3/13; H01R 13/582; Y10S 128/26
See application file for complete search history.

(56) References Cited

U.S. PATENT DOCUMENTS

| | | | |
|---|---|---|---|
| 3,760,811 A * | 9/1973 | Andrew | A61M 25/02 606/108 |
| 4,016,884 A | 4/1977 | Kwan-Gett | |
| 4,112,932 A | 9/1978 | Chiulli | |
| 4,183,357 A | 1/1980 | Bentley et al. | |
| 4,356,826 A | 11/1982 | Kubota | |
| 4,402,683 A | 9/1983 | Kopman | |
| 4,619,643 A | 10/1986 | Bai | |
| 4,653,476 A | 3/1987 | Bonnet | |
| 4,737,148 A | 4/1988 | Blake | |
| 4,863,430 A | 9/1989 | Klyce et al. | |
| 4,863,438 A | 9/1989 | Gauderer et al. | |
| 4,984,564 A | 1/1991 | Yuen | |
| 5,002,557 A | 3/1991 | Hasson | |
| 5,073,169 A | 12/1991 | Raiken | |
| 5,082,005 A | 1/1992 | Kaldany | |
| 5,122,122 A | 6/1992 | Allgood | |
| 5,159,921 A | 11/1992 | Hoover | |
| 5,176,697 A | 1/1993 | Hasson et al. | |
| 5,183,471 A | 2/1993 | Wilk | |
| 5,192,301 A | 3/1993 | Kamiya et al. | |
| 5,209,741 A | 5/1993 | Spaeth | |
| 5,209,754 A | 5/1993 | Ahluwalia | |
| 5,217,466 A | 6/1993 | Hasson | |
| 5,242,409 A | 9/1993 | Buelna | |
| 5,242,415 A | 9/1993 | Kantrowitz et al. | |
| 5,257,973 A | 11/1993 | Villasuso | |
| 5,257,975 A | 11/1993 | Foshee | |
| 5,269,772 A | 12/1993 | Wilk | |
| 5,271,380 A | 12/1993 | Riek et al. | |
| 5,290,245 A | 3/1994 | Dennis | |
| 5,290,249 A | 3/1994 | Foster et al. | |
| 5,308,336 A | 5/1994 | Hart et al. | |
| 5,312,391 A | 5/1994 | Wilk | |
| 5,312,417 A | 5/1994 | Wilk | |
| 5,314,417 A | 5/1994 | Stephens et al. | |
| 5,318,516 A | 6/1994 | Cosmescu | |
| 5,330,486 A | 7/1994 | Wilk | |
| 5,334,143 A | 8/1994 | Carroll | |
| 5,334,150 A | 8/1994 | Kaali | |
| 5,336,169 A | 8/1994 | Divilio et al. | |
| 5,336,203 A | 8/1994 | Goldhardt et al. | |
| 5,337,937 A | 8/1994 | Remiszewski et al. | |
| 5,345,927 A | 9/1994 | Bonutti | |
| 5,346,459 A | 9/1994 | Allen | |
| 5,360,417 A | 11/1994 | Gravener et al. | |
| 5,366,478 A | 11/1994 | Brinkerhoff et al. | |
| 5,375,588 A | 12/1994 | Yoon | |
| 5,378,588 A | 1/1995 | Tsuchiya | |
| 5,380,291 A | 1/1995 | Kaali | |
| 5,385,552 A | 1/1995 | Haber et al. | |
| 5,385,553 A | 1/1995 | Hart et al. | |
| 5,391,156 A | 2/1995 | Hildwein et al. | |
| 5,394,863 A | 3/1995 | Sanford et al. | |
| 5,395,367 A | 3/1995 | Wilk | |
| 5,407,433 A | 4/1995 | Loomas | |
| 5,431,151 A | 7/1995 | Riek et al. | |
| 5,437,683 A | 8/1995 | Neumann et al. | |
| 5,445,615 A | 8/1995 | Yoon | |
| 5,451,222 A | 9/1995 | De Maagd et al. | |
| 5,460,170 A | 10/1995 | Hammerslag | |
| 5,464,409 A | 11/1995 | Mohajer | |
| 5,480,410 A | 1/1996 | Cuschieri et al. | |
| 5,490,843 A | 2/1996 | Hildwein et al. | |
| 5,507,758 A | 4/1996 | Thomason et al. | |
| 5,511,564 A | 4/1996 | Wilk | |
| 5,514,133 A | 5/1996 | Golub et al. | |
| 5,514,153 A | 5/1996 | Bonutti | |
| 5,520,610 A | 5/1996 | Giglio et al. | |
| 5,520,698 A | 5/1996 | Koh | |
| 5,522,791 A | 6/1996 | Leyva | |
| 5,524,501 A | 6/1996 | Patterson et al. | |
| 5,524,644 A | 6/1996 | Crook | |
| 5,538,509 A | 7/1996 | Dunlap et al. | |
| 5,540,648 A | 7/1996 | Yoon | |
| 5,545,150 A | 8/1996 | Danks et al. | |
| 5,545,179 A | 8/1996 | Williamson, IV | |
| 5,549,565 A | 8/1996 | Ryan et al. | |
| 5,551,947 A | 9/1996 | Kaali | |
| 5,556,385 A | 9/1996 | Andersen | |
| 5,569,159 A | 10/1996 | Anderson et al. | |
| 5,569,205 A | 10/1996 | Hart et al. | |
| 5,569,291 A | 10/1996 | Privitera et al. | |
| 5,569,292 A | 10/1996 | Scwemberger et al. | |
| 5,577,993 A | 11/1996 | Zhu et al. | |
| 5,591,192 A | 1/1997 | Privitera et al. | |
| 5,601,581 A | 2/1997 | Fogarty et al. | |
| 5,609,562 A | 3/1997 | Kaali | |
| 5,624,399 A | 4/1997 | Ackerman | |
| 5,634,911 A | 6/1997 | Hermann et al. | |
| 5,634,937 A | 6/1997 | Mollenauer et al. | |
| 5,643,285 A | 7/1997 | Rowden et al. | |
| 5,649,550 A | 7/1997 | Crook | |
| 5,651,771 A | 7/1997 | Tangherlini et al. | |
| 5,653,705 A | 8/1997 | de la Torre et al. | |
| 5,656,013 A | 8/1997 | Yoon | |
| 5,672,168 A | 9/1997 | de la Torre et al. | |
| 5,683,378 A | 11/1997 | Christy | |
| 5,685,820 A | 11/1997 | Riek et al. | |
| 5,685,857 A | 11/1997 | Negus et al. | |
| 5,685,862 A | 11/1997 | Mahurkar | |
| 5,697,946 A | 12/1997 | Hopper et al. | |
| 5,709,671 A | 1/1998 | Stephens et al. | |
| 5,709,675 A | 1/1998 | Williams | |
| 5,713,858 A | 2/1998 | Heruth et al. | |
| 5,713,869 A | 2/1998 | Morejon | |
| 5,720,730 A | 2/1998 | Blake, III | |
| 5,720,761 A | 2/1998 | Kaali | |
| 5,722,962 A | 3/1998 | Garcia | |
| 5,728,103 A | 3/1998 | Picha et al. | |
| 5,730,748 A | 3/1998 | Fogarty et al. | |
| 5,735,791 A | 4/1998 | Alexander, Jr. et al. | |
| 5,741,298 A | 4/1998 | MacLeod | |
| 5,752,970 A | 5/1998 | Yoon | |
| 5,776,112 A | 7/1998 | Stephens et al. | |
| 5,782,817 A | 7/1998 | Franzel et al. | |
| 5,792,113 A | 8/1998 | Kramer et al. | |
| 5,795,290 A | 8/1998 | Bridges | |
| 5,800,451 A | 9/1998 | Buess et al. | |
| 5,803,921 A | 9/1998 | Bonadio | |
| 5,810,712 A | 9/1998 | Dunn | |
| 5,813,409 A | 9/1998 | Leahy et al. | |
| 5,830,191 A | 11/1998 | Hildwein et al. | |
| 5,836,871 A | 11/1998 | Wallace et al. | |
| 5,836,913 A | 11/1998 | Orth et al. | |
| 5,840,077 A | 11/1998 | Rowden et al. | |
| 5,842,971 A | 12/1998 | Yoon | |
| 5,848,992 A | 12/1998 | Hart et al. | |
| 5,853,417 A | 12/1998 | Fogarty et al. | |
| 5,857,461 A | 1/1999 | Levitsky et al. | |
| 5,865,817 A | 2/1999 | Moenning et al. | |
| 5,871,471 A | 2/1999 | Ryan et al. | |
| 5,871,474 A | 2/1999 | Hermann et al. | |
| 5,876,413 A | 3/1999 | Fogarty et al. | |
| 5,893,875 A | 4/1999 | O'Connor et al. | |
| 5,894,843 A | 4/1999 | Benetti et al. | |
| 5,895,377 A | 4/1999 | Smith et al. | |
| 5,899,208 A | 5/1999 | Bonadio | |
| 5,899,913 A | 5/1999 | Fogarty et al. | |
| 5,904,703 A | 5/1999 | Gilson | |
| 5,906,577 A | 5/1999 | Beane et al. | |
| 5,914,415 A | 6/1999 | Tago | |
| 5,916,198 A | 6/1999 | Dillow | |
| 5,941,898 A | 8/1999 | Moenning et al. | |
| 5,951,588 A | 9/1999 | Moenning | |
| 5,957,913 A | 9/1999 | de la Torre et al. | |
| 5,964,781 A | 10/1999 | Mollenauer et al. | |
| 5,976,174 A | 11/1999 | Ruiz | |

(56) References Cited

U.S. PATENT DOCUMENTS

| | | | |
|---|---|---|---|
| 5,997,515 | A | 12/1999 | de la Torre et al. |
| 6,007,481 | A | 12/1999 | Riek et al. |
| 6,017,355 | A | 1/2000 | Hessel et al. |
| 6,018,094 | A | 1/2000 | Fox |
| 6,024,736 | A | 2/2000 | de la Torre et al. |
| 6,030,402 | A | 2/2000 | Thompson et al. |
| 6,033,426 | A | 3/2000 | Kaji |
| 6,033,428 | A | 3/2000 | Sardella |
| 6,042,573 | A | 3/2000 | Lucey |
| 6,048,309 | A | 4/2000 | Flom et al. |
| 6,059,816 | A | 5/2000 | Moenning |
| 6,068,639 | A | 5/2000 | Fogarty et al. |
| 6,077,288 | A | 6/2000 | Shimomura et al. |
| 6,086,603 | A | 7/2000 | Termin et al. |
| 6,093,176 | A | 7/2000 | Dennis |
| 6,099,505 | A | 8/2000 | Ryan et al. |
| 6,099,506 | A | 8/2000 | Macoviak et al. |
| 6,110,154 | A | 8/2000 | Shimomura et al. |
| 6,142,936 | A | 11/2000 | Beane et al. |
| 6,156,006 | A | 12/2000 | Brosens et al. |
| 6,162,196 | A | 12/2000 | Hart et al. |
| 6,171,282 | B1 | 1/2001 | Ragsdale |
| 6,197,002 | B1 | 3/2001 | Peterson |
| 6,213,957 | B1 | 4/2001 | Milliman et al. |
| 6,217,555 | B1 | 4/2001 | Hart et al. |
| 6,228,063 | B1 | 5/2001 | Aboul-Hosn |
| 6,234,958 | B1 | 5/2001 | Snoke et al. |
| 6,238,373 | B1 | 5/2001 | de la Torre et al. |
| 6,241,768 | B1 | 6/2001 | Agarwal et al. |
| 6,251,119 | B1 | 6/2001 | Addis |
| 6,254,534 | B1 | 7/2001 | Butler et al. |
| 6,264,604 | B1 | 7/2001 | Kieturakis et al. |
| 6,276,661 | B1 | 8/2001 | Laird |
| 6,293,952 | B1 | 9/2001 | Brosens et al. |
| 6,315,770 | B1 | 11/2001 | de la Torre et al. |
| 6,319,246 | B1 | 11/2001 | de la Torre et al. |
| 6,328,720 | B1 | 12/2001 | McNally et al. |
| 6,329,637 | B1 | 12/2001 | Hembree et al. |
| 6,355,028 | B2 | 3/2002 | Castaneda et al. |
| 6,371,968 | B1 | 4/2002 | Kogasaka et al. |
| 6,382,211 | B1 | 5/2002 | Crook |
| 6,423,036 | B1 | 7/2002 | Van Huizen |
| 6,440,061 | B1 | 8/2002 | Wenner et al. |
| 6,440,063 | B1 | 8/2002 | Beane et al. |
| 6,443,957 | B1 | 9/2002 | Addis |
| 6,447,489 | B1 | 9/2002 | Peterson |
| 6,450,983 | B1 | 9/2002 | Rambo |
| 6,454,783 | B1 | 9/2002 | Piskun |
| 6,464,686 | B1 | 10/2002 | O'Hara et al. |
| 6,468,292 | B1 | 10/2002 | Mollenauer et al. |
| 6,478,806 | B2 | 11/2002 | McFarlane |
| 6,485,410 | B1 | 11/2002 | Loy |
| 6,485,467 | B1 | 11/2002 | Crook et al. |
| 6,487,806 | B2 | 12/2002 | Murello et al. |
| 6,488,620 | B1 | 12/2002 | Segermark et al. |
| 6,488,692 | B1 | 12/2002 | Spence et al. |
| 6,524,283 | B1 | 2/2003 | Hopper et al. |
| 6,527,787 | B1 | 3/2003 | Fogarty et al. |
| 6,544,210 | B1 | 4/2003 | Trudel et al. |
| 6,551,270 | B1 | 4/2003 | Bimbo et al. |
| 6,551,282 | B1 | 4/2003 | Exline et al. |
| 6,558,371 | B2 | 5/2003 | Dorn |
| 6,562,022 | B2 | 5/2003 | Hoste et al. |
| 6,569,120 | B1 | 5/2003 | Green et al. |
| 6,572,631 | B1 | 6/2003 | McCartney |
| 6,578,577 | B2 | 6/2003 | Bonadio et al. |
| 6,582,364 | B2 | 6/2003 | Butler et al. |
| 6,589,167 | B1 | 7/2003 | Shimomura et al. |
| 6,589,316 | B1 | 7/2003 | Schultz et al. |
| 6,592,543 | B1 | 7/2003 | Wortrich et al. |
| 6,613,038 | B2 | 9/2003 | Bonutti et al. |
| 6,613,952 | B2 | 9/2003 | Rambo |
| 6,623,426 | B2 | 9/2003 | Bonadio et al. |
| 6,669,674 | B1 | 12/2003 | Macoviak et al. |
| 6,676,639 | B1 | 1/2004 | Ternstrom |
| 6,684,405 | B2 | 2/2004 | Lezdey |
| 6,702,787 | B2 | 3/2004 | Racenet et al. |
| 6,706,050 | B1 | 3/2004 | Giannadakis |
| 6,716,201 | B2 | 4/2004 | Blanco |
| 6,723,044 | B2 | 4/2004 | Pulford et al. |
| 6,723,088 | B2 | 4/2004 | Gaskill, III et al. |
| 6,725,080 | B2 | 4/2004 | Melkent et al. |
| 6,736,797 | B1 | 5/2004 | Larsen et al. |
| 6,740,064 | B1 | 5/2004 | Sorrentino et al. |
| 6,800,084 | B2 | 10/2004 | Davison et al. |
| 6,811,546 | B1 | 11/2004 | Callas et al. |
| 6,814,078 | B2 | 11/2004 | Crook |
| 6,830,578 | B2 | 12/2004 | O'Heeron et al. |
| 6,835,201 | B2 | 12/2004 | O'Heeron et al. |
| 6,837,893 | B2 | 1/2005 | Miller |
| 6,840,946 | B2 | 1/2005 | Fogarty et al. |
| 6,840,951 | B2 | 1/2005 | de la Torre et al. |
| 6,846,287 | B2 | 1/2005 | Bonadio et al. |
| 6,855,128 | B2 | 2/2005 | Swenson |
| 6,863,674 | B2 | 3/2005 | Kasahara et al. |
| 6,878,110 | B2 | 4/2005 | Yang et al. |
| 6,884,253 | B1 | 4/2005 | McFarlane |
| 6,890,295 | B2 | 5/2005 | Michels et al. |
| 6,913,609 | B2 | 7/2005 | Yencho et al. |
| 6,916,310 | B2 | 7/2005 | Sommerich |
| 6,916,331 | B2 | 7/2005 | Mollenauer et al. |
| 6,929,637 | B2 | 8/2005 | Gonzalez et al. |
| 6,939,296 | B2 | 9/2005 | Ewers et al. |
| 6,942,633 | B2 | 9/2005 | Odland |
| 6,942,671 | B1 | 9/2005 | Smith |
| 6,945,932 | B1 | 9/2005 | Caldwell et al. |
| 6,958,037 | B2 | 10/2005 | Ewers et al. |
| 6,960,164 | B2 | 11/2005 | O'Heeron |
| 6,972,026 | B1 | 12/2005 | Caldwell et al. |
| 6,986,752 | B2 | 1/2006 | McGuckin, Jr. et al. |
| 6,991,602 | B2 | 1/2006 | Nakazawa et al. |
| 6,997,909 | B2 | 2/2006 | Goldberg |
| 7,001,397 | B2 | 2/2006 | Davison et al. |
| 7,008,377 | B2 | 3/2006 | Beane et al. |
| 7,011,645 | B2 | 3/2006 | McGuckin, Jr. et al. |
| 7,014,628 | B2 | 3/2006 | Bousquet |
| 7,033,319 | B2 | 4/2006 | Pulford et al. |
| 7,052,454 | B2 | 5/2006 | Taylor |
| 7,056,321 | B2 | 6/2006 | Pagliuca et al. |
| 7,077,852 | B2 | 7/2006 | Fogarty et al. |
| 7,081,089 | B2 | 7/2006 | Bonadio et al. |
| 7,083,626 | B2 | 8/2006 | Hart et al. |
| 7,100,614 | B2 | 9/2006 | Stevens et al. |
| 7,101,353 | B2 | 9/2006 | Lui et al. |
| 7,104,981 | B2 | 9/2006 | Elkins et al. |
| 7,153,261 | B2 | 12/2006 | Wenchell |
| 7,160,309 | B2 | 1/2007 | Voss |
| 7,163,510 | B2 | 1/2007 | Kahle et al. |
| 7,192,436 | B2 | 3/2007 | Sing et al. |
| 7,195,590 | B2 | 3/2007 | Butler et al. |
| 7,201,725 | B1 | 4/2007 | Cragg et al. |
| 7,214,185 | B1 | 5/2007 | Rosney et al. |
| 7,217,277 | B2 | 5/2007 | Parihar et al. |
| 7,223,257 | B2 | 5/2007 | Shubayev et al. |
| 7,223,278 | B2 | 5/2007 | Davison et al. |
| 7,235,064 | B2 | 6/2007 | Hopper et al. |
| 7,235,084 | B2 | 6/2007 | Skakoon et al. |
| 7,238,154 | B2 | 7/2007 | Ewers et al. |
| 7,258,712 | B2 | 8/2007 | Schultz et al. |
| 7,276,075 | B1 | 10/2007 | Callas et al. |
| 7,294,103 | B2 | 11/2007 | Bertolero et al. |
| 7,300,399 | B2 | 11/2007 | Bonadio et al. |
| 7,300,448 | B2 | 11/2007 | Criscuolo et al. |
| 7,316,699 | B2 | 1/2008 | McFarlane |
| 7,320,694 | B2 | 1/2008 | O'Heeron |
| 7,331,940 | B2 | 2/2008 | Sommerich |
| 7,344,547 | B2 | 3/2008 | Piskun |
| 7,370,694 | B2 | 5/2008 | Shimizu et al. |
| 7,377,898 | B2 | 5/2008 | Ewers et al. |
| 7,390,322 | B2 | 6/2008 | McGuckin, Jr. et al. |
| 7,393,322 | B2 | 7/2008 | Wenchell |
| 7,412,977 | B2 | 8/2008 | Fields et al. |
| 7,440,661 | B2 | 10/2008 | Kobayashi |
| 7,445,597 | B2 | 11/2008 | Butler et al. |

(56) References Cited

U.S. PATENT DOCUMENTS

| | | |
|---|---|---|
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,494,481 B2 | 2/2009 | Moberg et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,678,046 B2 | 3/2010 | White et al. |
| 7,686,823 B2 | 3/2010 | Pingleton et al. |
| 7,704,207 B2 | 4/2010 | Albrecht et al. |
| 7,708,713 B2 | 5/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,744,569 B2 | 6/2010 | Smith |
| 7,753,901 B2 | 7/2010 | Piskun et al. |
| 7,758,500 B2 | 7/2010 | Boyd et al. |
| 7,758,603 B2 | 7/2010 | Taylor et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,794,644 B2 | 9/2010 | Taylor et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,655 B2 | 12/2010 | Pasqualucci |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,918,827 B2 | 4/2011 | Smith |
| 7,947,058 B2 | 5/2011 | Kahle et al. |
| 7,951,076 B2 | 5/2011 | Hart et al. |
| 7,955,257 B2 | 6/2011 | Frasier et al. |
| 7,955,313 B2 | 6/2011 | Boismier |
| 7,985,232 B2 | 7/2011 | Potter et al. |
| 3,002,750 A1 | 8/2011 | Smith |
| 3,002,786 A1 | 8/2011 | Beckman et al. |
| 7,998,068 B2 | 8/2011 | Bonadio et al. |
| 3,012,128 A1 | 9/2011 | Franer et al. |
| 3,021,296 A1 | 9/2011 | Bonadio et al. |
| 8,025,670 B2 | 9/2011 | Sharp et al. |
| 8,029,475 B2 | 10/2011 | Franer et al. |
| 8,038,652 B2 | 10/2011 | Morrison et al. |
| 8,052,653 B2 | 11/2011 | Gratwohl et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,092,431 B2 | 1/2012 | Lunn et al. |
| 8,105,234 B2 | 1/2012 | Ewers et al. |
| 8,109,873 B2 | 2/2012 | Albrecht et al. |
| 8,118,735 B2 | 2/2012 | Voegele |
| 8,128,590 B2 | 3/2012 | Albrecht et al. |
| 8,137,318 B2 | 3/2012 | Schweitzer et al. |
| 8,147,453 B2 | 4/2012 | Albrecht et al. |
| 8,152,828 B2 | 4/2012 | Taylor et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,206,411 B2 | 6/2012 | Thompson et al. |
| 8,241,209 B2 | 8/2012 | Shelton, IV et al. |
| 8,262,568 B2 | 9/2012 | Albrecht et al. |
| 8,267,952 B2 | 9/2012 | Kahle et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,398,666 B2 | 3/2013 | McFarlane |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 8,597,180 B2 | 12/2013 | Copeland et al. |
| 8,961,406 B2 | 2/2015 | Ortiz et al. |
| 10,022,149 B2 | 7/2018 | Holsten et al. |
| 2001/0037053 A1 | 11/2001 | Bonadio et al. |
| 2002/0055714 A1 | 5/2002 | Rothschild |
| 2002/0091410 A1 | 7/2002 | Ben-David et al. |
| 2002/0173748 A1 | 11/2002 | McConnell et al. |
| 2003/0014076 A1 | 1/2003 | Mollenauer et al. |
| 2003/0093104 A1 | 5/2003 | Bonner et al. |
| 2003/0109853 A1 | 6/2003 | Harding et al. |
| 2003/0153926 A1 | 8/2003 | Schmieding et al. |
| 2003/0187376 A1 | 10/2003 | Rambo |
| 2003/0187397 A1 | 10/2003 | Vitali |
| 2003/0233115 A1 | 12/2003 | Eversull et al. |
| 2003/0236549 A1 | 12/2003 | Bonadio et al. |
| 2004/0006356 A1 | 1/2004 | Smith |
| 2004/0054353 A1 | 3/2004 | Taylor |
| 2004/0059297 A1 | 3/2004 | Racenet et al. |
| 2004/0073090 A1 | 4/2004 | Butler et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0186434 A1 | 9/2004 | Harding et al. |
| 2004/0204682 A1 | 10/2004 | Smith |
| 2004/0204734 A1 | 10/2004 | Wagner et al. |
| 2004/0215209 A1 | 10/2004 | Almond et al. |
| 2004/0267096 A1 | 12/2004 | Caldwell et al. |
| 2004/0267204 A1 | 12/2004 | Brustowicz |
| 2005/0010238 A1 | 1/2005 | Potter et al. |
| 2005/0020884 A1 | 1/2005 | Hart et al. |
| 2005/0033342 A1 | 2/2005 | Hart et al. |
| 2005/0070850 A1 | 3/2005 | Albrecht |
| 2005/0070851 A1 | 3/2005 | Thompson et al. |
| 2005/0070935 A1 | 3/2005 | Ortiz |
| 2005/0070946 A1 | 3/2005 | Franer et al. |
| 2005/0070947 A1 | 3/2005 | Franer et al. |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0192594 A1 | 9/2005 | Skakoon et al. |
| 2005/0203346 A1 | 9/2005 | Bonadio et al. |
| 2005/0209608 A1 | 9/2005 | O'Heeron |
| 2005/0212221 A1 | 9/2005 | Smith et al. |
| 2005/0222582 A1 | 10/2005 | Wenchell |
| 2005/0245876 A1 | 11/2005 | Khosravi et al. |
| 2005/0251092 A1 | 11/2005 | Howell et al. |
| 2005/0251190 A1 | 11/2005 | McFarlane |
| 2005/0277946 A1 | 12/2005 | Greenhalgh |
| 2006/0020281 A1 | 1/2006 | Smith |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0211992 A1 | 9/2006 | Prosek |
| 2006/0212063 A1 | 9/2006 | Wilk |
| 2006/0217665 A1 | 9/2006 | Prosek |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |

(56) References Cited

U.S. PATENT DOCUMENTS

| | | |
|---|---|---|
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2006/0276751 A1 | 12/2006 | Haberland et al. |
| 2007/0088277 A1 | 4/2007 | McGinley et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0185453 A1 | 8/2007 | Michael et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0239108 A1 | 10/2007 | Albrecht et al. |
| 2007/0255218 A1 | 11/2007 | Franer |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0051739 A1 | 2/2008 | McFarlane |
| 2008/0058723 A1 | 3/2008 | Lipchitz et al. |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0146884 A1 | 6/2008 | Beckman et al. |
| 2008/0161758 A1 | 7/2008 | Insignares |
| 2008/0161826 A1 | 7/2008 | Guiraudon |
| 2008/0177265 A1 | 7/2008 | Lechot |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0202529 A1* | 8/2008 | Flory ............... A61M 16/0488 128/207.17 |
| 2008/0208222 A1 | 8/2008 | Beckman et al. |
| 2008/0249475 A1 | 10/2008 | Albrecht et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093835 A1 | 4/2009 | Heinrich et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182282 A1 | 7/2009 | Okihisa et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0234293 A1 | 9/2009 | Albrecht et al. |
| 2009/0275880 A1 | 11/2009 | Pasqualucci |
| 2009/0326330 A1 | 12/2009 | Bonadio et al. |
| 2009/0326332 A1 | 12/2009 | Carter |
| 2010/0010449 A1* | 1/2010 | Leibowitz .......... A61B 17/3421 604/179 |
| 2010/0016800 A1 | 1/2010 | Rockrohr |
| 2010/0030155 A1 | 2/2010 | Gyrn et al. |
| 2010/0049138 A1 | 2/2010 | Smith et al. |
| 2010/0063450 A1 | 3/2010 | Smith et al. |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0222801 A1 | 9/2010 | Pingleton et al. |
| 2010/0228090 A1 | 9/2010 | Weisenburgh, II |
| 2010/0228094 A1 | 9/2010 | Ortiz et al. |
| 2010/0228096 A1 | 9/2010 | Weisenburgh, II et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0261975 A1 | 10/2010 | Huey et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0286706 A1 | 11/2010 | Judson |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0087159 A1 | 4/2011 | Parihar et al. |
| 2011/0087168 A1 | 4/2011 | Parihar et al. |
| 2011/0087169 A1 | 4/2011 | Parihar et al. |
| 2011/0118553 A1 | 5/2011 | Stopek |
| 2011/0118833 A1 | 5/2011 | Reichenbach et al. |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0190592 A1 | 8/2011 | Kahle et al. |
| 2011/0201891 A1 | 8/2011 | Smith et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0251559 A1 | 10/2011 | Tal et al. |
| 2011/0251560 A1 | 10/2011 | Albrecht et al. |
| 2011/0251633 A1 | 10/2011 | Smith |
| 2011/0276002 A1 | 11/2011 | Bierman |
| 2011/0313250 A1 | 12/2011 | Kleyman |
| 2012/0010569 A1 | 1/2012 | Parihar |
| 2012/0041371 A1 | 2/2012 | Tal et al. |
| 2012/0059640 A1 | 3/2012 | Roy et al. |
| 2012/0065590 A1 | 3/2012 | Bierman et al. |
| 2012/0109064 A1 | 5/2012 | Fischvogt et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2012/0316596 A1 | 12/2012 | Taylor et al. |

(56) References Cited

U.S. PATENT DOCUMENTS

| | | |
|---|---|---|
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2014/0371537 A1 | 12/2014 | Marczyk et al. |
| 2015/0025477 A1 | 1/2015 | Evans |
| 2015/0065808 A1 | 3/2015 | Van Wyk et al. |
| 2015/0223833 A1 | 8/2015 | Coffeen et al. |

FOREIGN PATENT DOCUMENTS

| | | |
|---|---|---|
| DE | 202008009527 U1 | 10/2008 |
| EP | 0226026 A2 | 6/1987 |
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 1994896 A1 | 11/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2145593 A1 | 1/2010 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| GB | 2469083 | 4/2009 |
| JP | 2001525693 A | 12/2001 |
| JP | 2004532660 A | 10/2004 |
| JP | 2006187603 A | 7/2006 |
| JP | 2008289889 A | 12/2008 |
| JP | 2009534124 A | 9/2009 |
| JP | 2011515128 A | 5/2011 |
| WO | 8401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 | 9/1997 |
| WO | 9742889 | 11/1997 |
| WO | 9850093 A1 | 11/1998 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2006118650 A1 | 11/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |
| WO | 2014116889 A1 | 7/2014 |
| WO | 2016094653 A1 | 6/2016 |
| WO | 2016186905 A1 | 11/2016 |
| WO | 2018024101 A1 | 2/2018 |

OTHER PUBLICATIONS

European Office Action dated Feb. 8, 2023, issued in corresponding EP Application No. 21 270 137, 5 pages.

* cited by examiner

ACCESS ASSEMBLY WITH RETENTION MECHANISM

FIELD

The present disclosure relates generally to a surgical access assembly having an anchor mechanism to securely engage tissue to prevent withdrawal of the surgical access assembly from the tissue, e.g., the abdominal wall, and, in particular, relates to an access assembly further including a retention mechanism for preventing over-insertion of the surgical access assembly into the body cavity.

BACKGROUND

Minimally invasive surgical procedures including both endoscopic and laparoscopic procedures permit surgery to be performed on organs, tissues and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula accessing the abdominal cavity to perform one or more surgical tasks. The cannula may incorporate a seal to establish a substantially fluid tight seal about the instrument to preserve the integrity of the pneumoperitoneum.

While minimally invasive surgical procedures have proven to be quite effective in surgery, limitations remain. For example, the cannula which is subjected to the pressurized environment, i.e., the pneumoperitoneum, may have a tendency to back out of the incision in the abdominal wall particularly during multiple manipulations of the instrument within the cannula. Conversely, during insertion and/or manipulation of instruments through the cannula, the cannula may become over-inserted, risking damage to the internal organs.

SUMMARY

A retention mechanism for a surgical access assembly is provided. The retention mechanism includes a planar base having first and second extensions each with a free end, a first locking member disposed on the free end of the first extension, and a second locking member disposed on the free end of the second extension. The first locking member includes a U-shaped body having a first set of opposed, inwardly facing teeth. The second locking member includes a U-shaped body having a first set of opposed, outwardly facing teeth configured engage the first set of opposed, inwardly facing teeth when the retention mechanism is in a locked condition. The first set of opposed, inwardly facing teeth and the first set of opposed, outwardly facing teeth are configured to be spaced apart from each other when the retention mechanism is in an unlocked condition.

In certain aspects of the disclosure, the first locking member includes a snap member disposed adjacent the first set of opposed, inwardly facing teeth and the second locking member includes a locking portion defining a recess for receiving the snap member of the first locking member. Receipt of the snap member through the recess of the locking portion may secure the first and second locking members relative to each other. The first locking member may include a second set of opposed, inwardly facing teeth and the second locking member may include a second set of opposed, outwardly facing teeth releasably engageable with the second set of opposed, inwardly facing teeth of the first locking member.

In some aspects of the disclosure, the first locking member includes a snap member disposed between each of the first and second sets of opposed, inwardly facing teeth, and the second locking member includes a locking portion defining a recess disposed between each of the first and second sets of opposed, outwardly facing teeth of the second locking member. The snap members may be configured to be received within the recess of the locking portions to secure the first locking member relative to the second locking member. Receipt of the snap members within the recess of the locking portions may secure the first and second locking members relative to each other.

In aspects of the disclosure, the second locking member includes button members for facilitating movement of the first set of opposed, outwardly facing teeth relative to the first set of opposed, inwardly facing teeth. Each of the first and second extensions may include a narrow portion to permit folding of the respective first and second extensions relative to the planar base. The first and second extensions may be configured to receive sutures.

A surgical access assembly including a cannula having a distal portion and a length, an anchor mechanism disposed on the distal portion of the cannula, and a retention mechanism receivable about the length of the cannula. The retention mechanism includes a first locking member including a U-shaped body having a first set of opposed, inwardly facing teeth, and a second locking member including a U-shaped body having a first set of opposed, outwardly facing teeth configured to engage the first set of opposed, inwardly facing teeth when the retention mechanism is in a locked condition and to be spaced apart from the first set of opposed, inwardly facing teeth when the retention mechanism is in an unlocked condition.

In some aspects of the disclosure, the first locking member includes a snap member disposed adjacent the first set of opposed, inwardly facing teeth and the second locking member includes a locking portion defining a recess for receiving the snap member of the first locking member. Receipt of the snap member through the recess of the locking portion may secure the first and second locking members relative to each other. The first locking member may include a second set of opposed, inwardly facing teeth and the second locking member may include a second set of opposed, outwardly facing teeth releasably engageable with the second set of opposed, inwardly facing teeth of the first locking member.

In certain aspects of the disclosure, the first locking member includes a snap member disposed between each of the first and second sets of opposed, inwardly facing teeth, and the second locking member includes a locking portion defining a recess disposed between each of the first and second sets of opposed, outwardly facing teeth of the second locking member. The snap members may be configured to be received within the recess of the locking portions to secure the first locking member relative to the second locking member. Receipt of the snap members within the recess of the locking portions may secure the first and second locking members relative to each other.

In aspects of the disclosure, the second locking member includes button members for facilitating movement of the first set of opposed, outwardly facing teeth relative to the first set of opposed, inwardly facing teeth. The anchor mechanism may include an inflatable balloon. The surgical access assembly may further include a foam block positionable about the cannula between the anchor mechanism and the retention mechanism.

BRIEF DESCRIPTION OF THE DRAWINGS

Various aspects and features of the present disclosure are described hereinbelow with references to the drawings, wherein.

DETAILED DESCRIPTION

Figure 1:
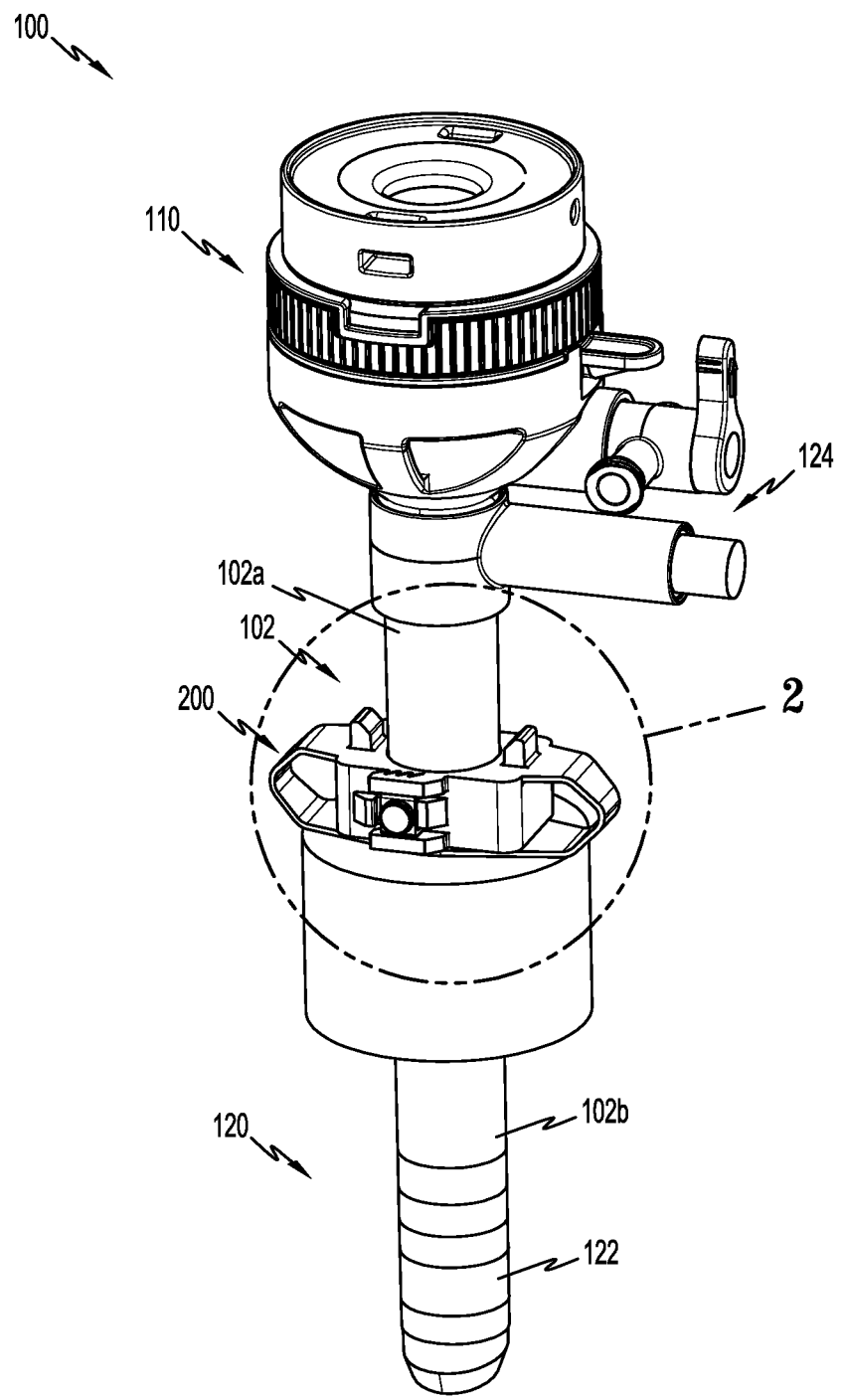
FIG. 1 is a perspective view of an access assembly according to an aspect of the present disclosure including a retention mechanism.
Figure 2:
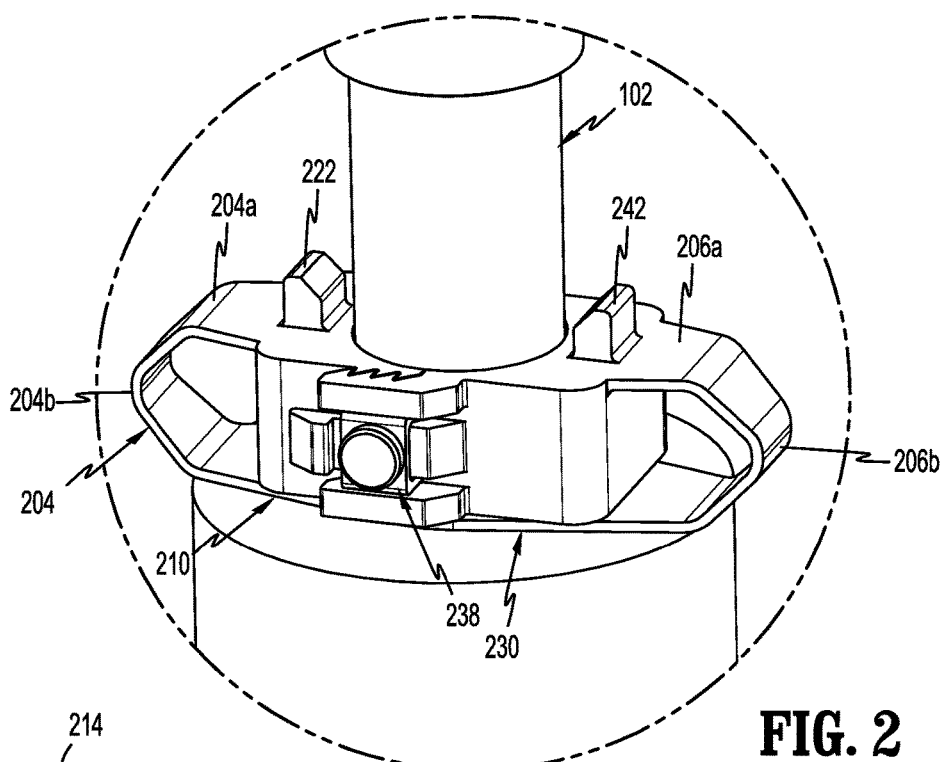
FIG. 2 is an enlarged view of the indicated area of detail in FIG. 1.
Figure 3:
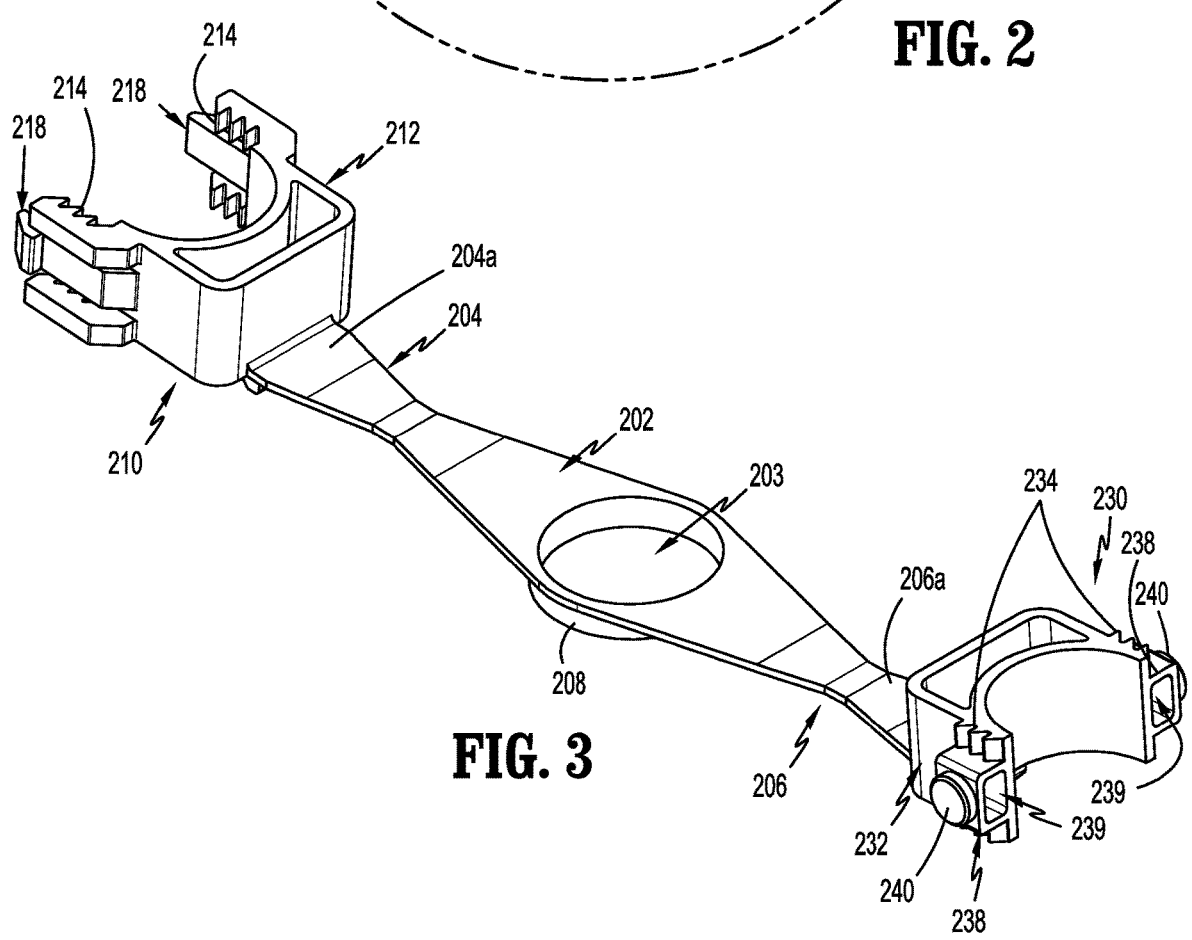
FIG. 3 is a top perspective view of the retention mechanism shown in FIG. 1, in an unfolded condition.
Figure 4:
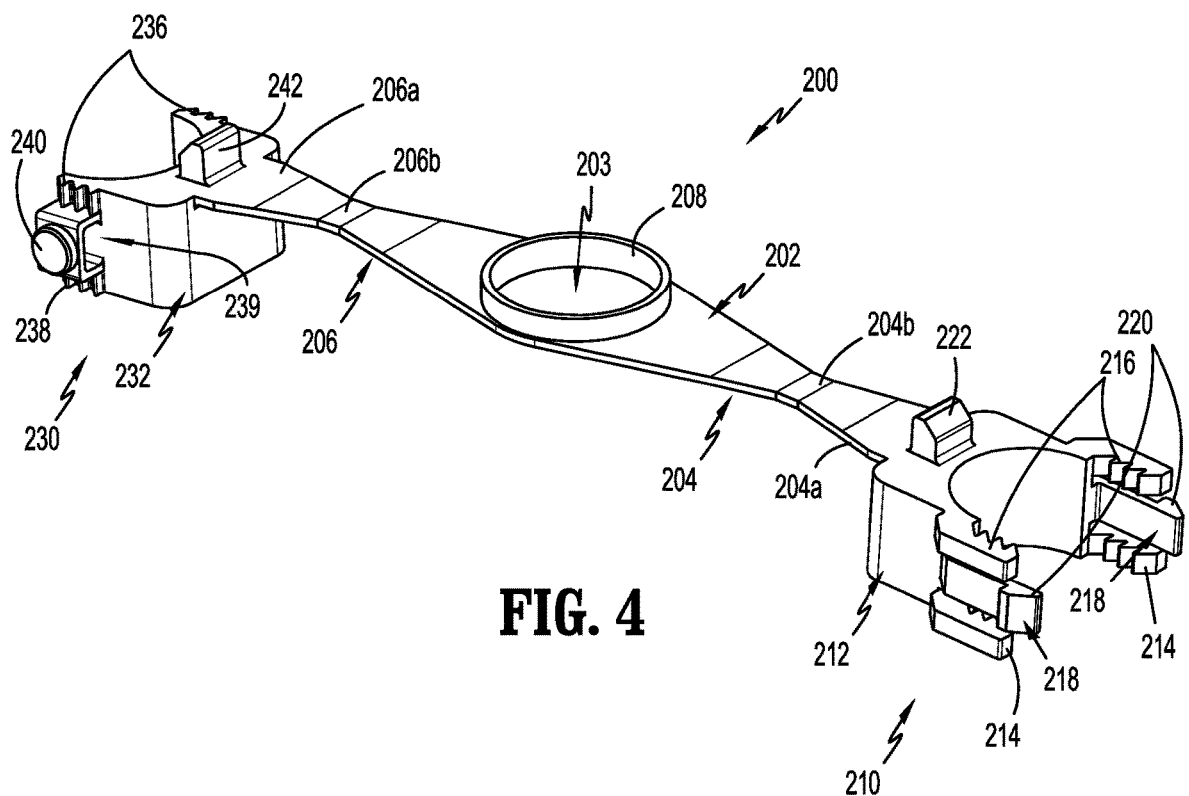
FIG. 4 is a bottom perspective view of the retention mechanism shown in FIGS. 1 and 2, in the unfolded condition.
Figure 5:
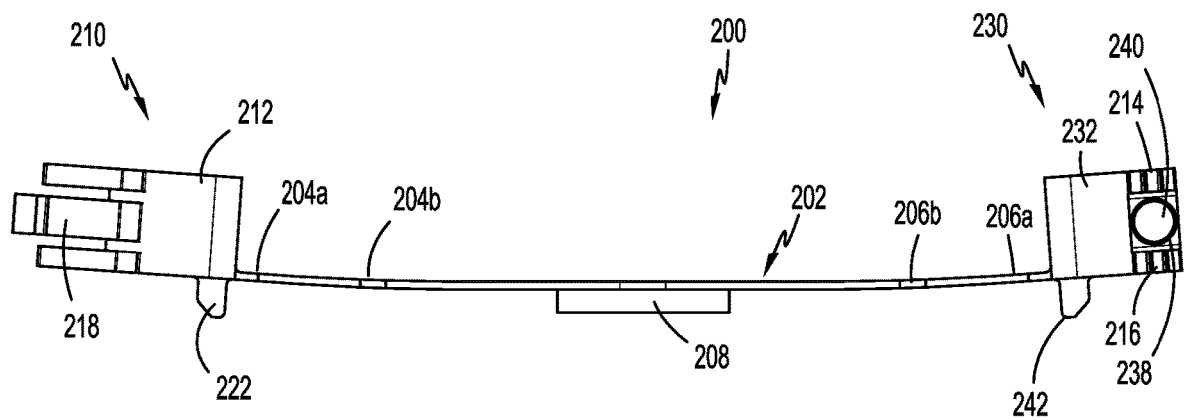
FIG. 5 is a side view of the retention mechanism shown in FIGS. 1-4, in the unfolded condition.

Particular access assemblies in accordance with the disclosure are described hereinbelow with reference to the accompanying drawings; however, it is to be understood that the disclosed access assemblies are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user.

Access assemblies with obturators are employed during minimally invasive surgery, e.g., laparoscopic surgery, and provide for the sealed access of surgical instruments into an insufflated body cavity, such as the abdominal cavity. The access assemblies typically include an instrument valve housing mounted on a cannula tube, and include an obturator (not shown) inserted through the valve housing and cannula. The obturator can have a blunt distal end, or a bladed or non-bladed penetrating distal end and can be used to incise the abdominal wall so that the access assembly can be introduced into the abdomen. The handle of the obturator can engage or selectively lock into the instrument valve housing of the access assembly.

Trocar assemblies are employed to tunnel through an anatomical structure, e.g., the abdominal wall, either by making a new passage through the anatomical structure or by passing through an existing opening through the anatomical structure. Once the trocar assembly with the obturator has tunneled through the anatomical structure, the obturator is removed, leaving the access assembly in place. The instrument valve housing of the access assembly includes valves that prevent the escape of insufflation gases from the body cavity, while also allowing surgical instruments to be inserted into the cavity.

Many access assemblies include an anchor mechanism for preventing withdrawal of the access assembly. These anchor mechanisms may be in the form of an inflatable balloon. Alternatively, the access assemblies may be maintained in position with an expandable flange or other structure capable of being collapsed to facilitate insertion of the access assembly through the tissue and selectively expanded to prevent withdrawal of the access assembly from the tissue.

FIG. 1 illustrates an access assembly 100 suitable for use with a retention mechanism according to exemplary aspects of the disclosure. The access assembly 100 includes a cannula 102 and an instrument valve housing 110 supported to a proximal portion 102a of the cannula 102. Although shown including the instrument valve housing 110, it is envisioned that retention mechanisms in accordance with the disclosure may be incorporated into access assemblies without an instrument valve housing 110.

Figure 15:
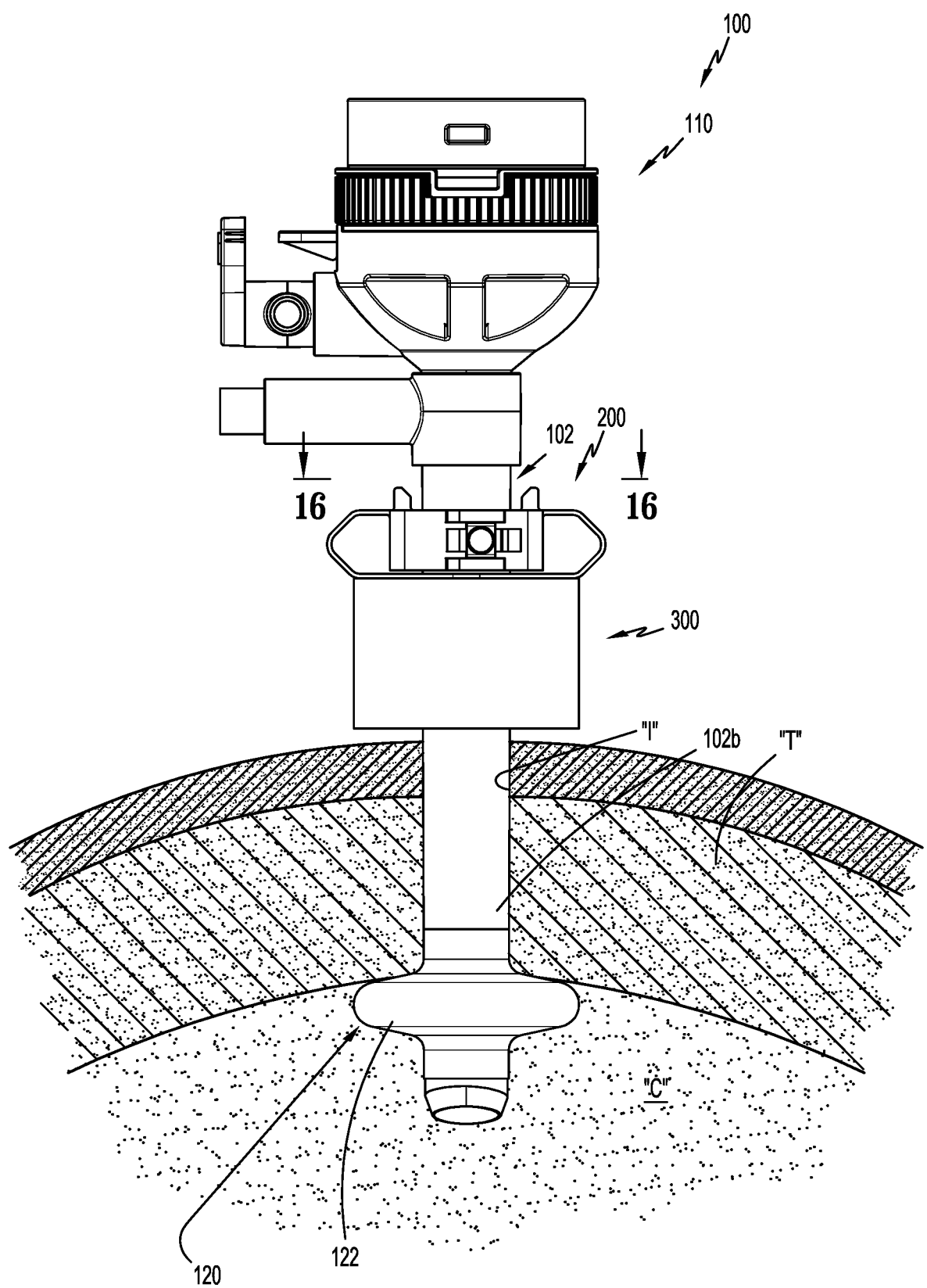
FIG. 15 is a side view of the access assembly shown in FIG. 1, operably engaged with tissue "T" and with the first and second locking members of the retention mechanism in the locked condition.

The access assembly 100 includes an anchor mechanism 120 supported on a distal portion 102b of the cannula 102. As shown, the anchor mechanism 120 includes a balloon anchor 122. The balloon anchor 122 includes an uninflated or collapsed condition (FIG. 1) and an inflated or expanded condition (FIG. 15). The balloon anchor 122 is inflatable through a port 124 supported on the proximal portion 102a of the cannula 102. The anchor mechanism 120 will only be described herein to the extent necessary to disclose the features of the retention mechanisms of the present disclosure. For detailed descriptions of the structure and function of exemplary anchor assemblies suitable for use with the access assemblies the present disclosure, please refer to U.S. Pat. Nos. 5,697,946, 7,691,089, and 10,327,809, and U.S. Pat. App. Pub. No. 2004/0138702. Although features of the retention mechanisms of the present disclosure will be shown and described with reference to a balloon anchor, it is envisioned that the retention mechanisms of the disclosure may be used with access assemblies having various anchor mechanism, including, for example, a collapsible flange.

The access assembly 100 also includes a retention mechanism 200. The retention mechanism 200 operates in combination with the anchor mechanism 120 to support the access assembly 100 within tissue "T" (FIG. 15).

FIGS. 2-5 illustrate the retention mechanism 200 in detail. The retention mechanism 200 is configured to frictionally engage the cannula 102 of the access assembly 100 to prevent over-insertion of the access assembly 100 through the tissue during receipt and or manipulation of a surgical instrument (not shown) through the access assembly 100. As will be described in further detail below, the retention mechanism 200 is configured to permit adjustment of the position of the retention mechanism 200 along the length of the cannula 102 of the access assembly 100. In certain aspects of the disclosure, the retention mechanism 200 is formed from a flexible and/or resilient plastic material.

The retention mechanism 200 includes a planar base 202 having first and second extensions 204, 206. The planar base 202 defines a circular opening 203 and includes an annular flange 208 formed about the circular opening 203. The circular opening 203 is sized to receive the cannula 102 of the access assembly 100. A first locking member 210 is disposed on a free end 204a of the first extension 204 and a second locking member 230 is disposed on a free end 206a of the second extension 206. Each of the first and second extensions 204, 206 includes a narrow portion 204b, 206b, respectively, for facilitating folding of the respective first and second extensions 204, 206 to permit engagement of the first locking member 210 with the second locking member 230.

The first locking member 210 of the retention mechanism 200 includes a substantially U-shaped base 212. Free ends of the U-shaped base 212 include first and second sets of opposed, inwardly facing teeth 214 (FIG. 3), 216 (FIG. 4), and a snap lock 218 disposed between each of the first and second sets of opposed, inwardly facing teeth 214, 216. The snap locks 218 include a locking tab 220 on a free end of each of the snap locks 218. The first locking member 210 further includes an engagement member 222 extending outwardly from the U-shaped base 212 configured for engagement by a user.

The second locking member 230 of the retention mechanism 200 includes a substantially U-shaped base 232. Free ends of the U-shaped base 232 include first and second sets of opposed, outwardly facing teeth 234 (FIG. 3), 236 (FIG. 4) corresponding to the first and second sets of opposed, inwardly facing teeth 214, 216 of the first locking member 210, and a locking portion 238 disposed between each of the first and second opposed, outwardly facing teeth 234, 236. Each of the locking portions 238 defines a recess 239 for receiving the snap locks 218 of the first locking member 210. A button member 240 is disposed on each of the locking portions 238 of the second locking member 230. As will be described in further detail below, the button members 240 on each of the locking portions 238 permit flexing of the first and second sets of opposed, outwardly facing teeth 234, 236 away from the first and second sets of opposed, inwardly facing teeth 214, 216 of the first locking member 210 to allow movement of the first locking member 210 relative to the second locking member 230. The second locking member 230 further includes an engagement member 242 extending outwardly from the U-shaped base 232. The engagement member 222 of the first locking member 210 and the engagement member 242 of the second locking member 230 are configured to be engaged by a user and facilitate movement of the first and second locking members 210, 230 relative to each other.

The assembly and operation of the retention mechanism 200 will now be described with reference to FIGS. 6-14.

Figure 6:
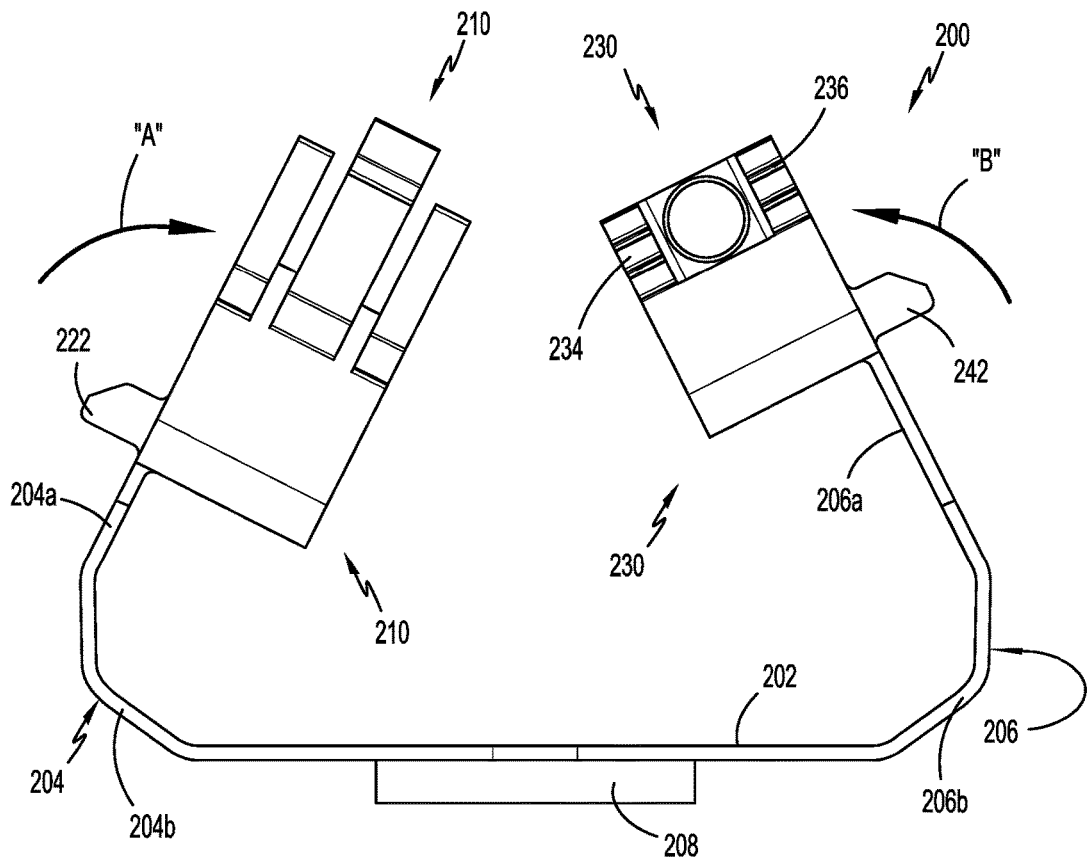
FIG. 6 is a side view of the retention mechanism shown in FIGS. 1-5, in a partially folded condition.

FIG. 6 illustrates folding of the first and second locking members 210, 230 of the retention mechanism 200 relative to the planar body 202 of the retention mechanism 200, as indicated by arrows "A" and "B", respectively, along the narrow portions 204b, 206b of the respective first and second extensions 204, 206 of the retention mechanism 200.

Figure 7:
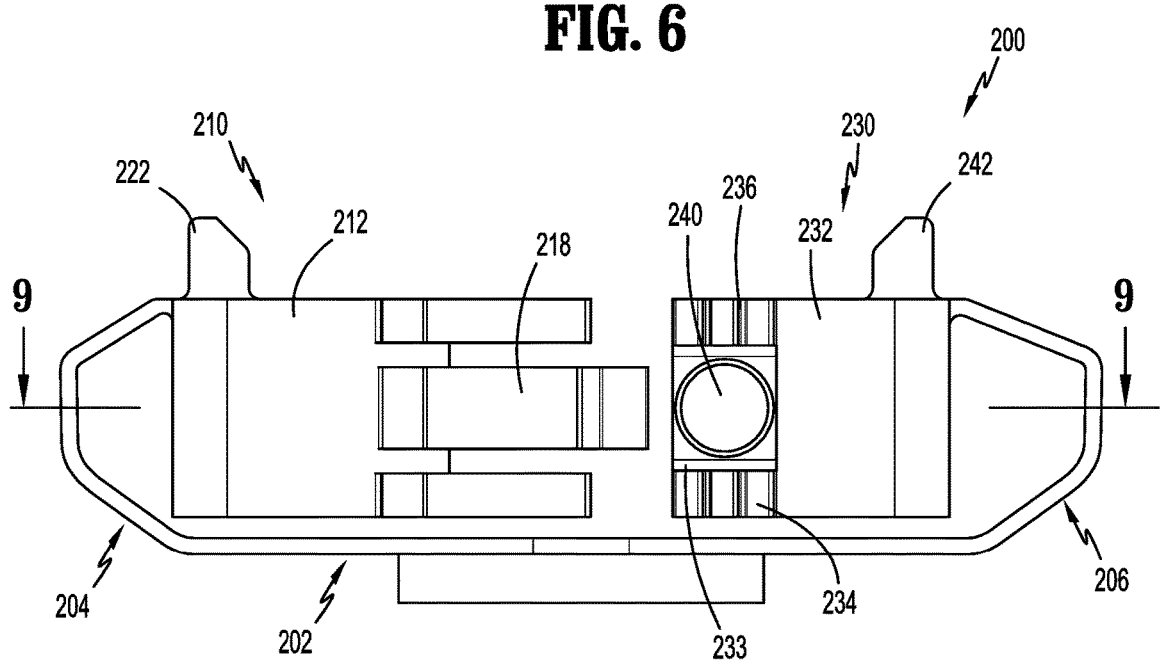
FIG. 7 is a side view of the retention mechanism shown in FIGS. 1-6, in a folded condition and with first and second locking members of the retention mechanism spaced apart.
Figure 8:
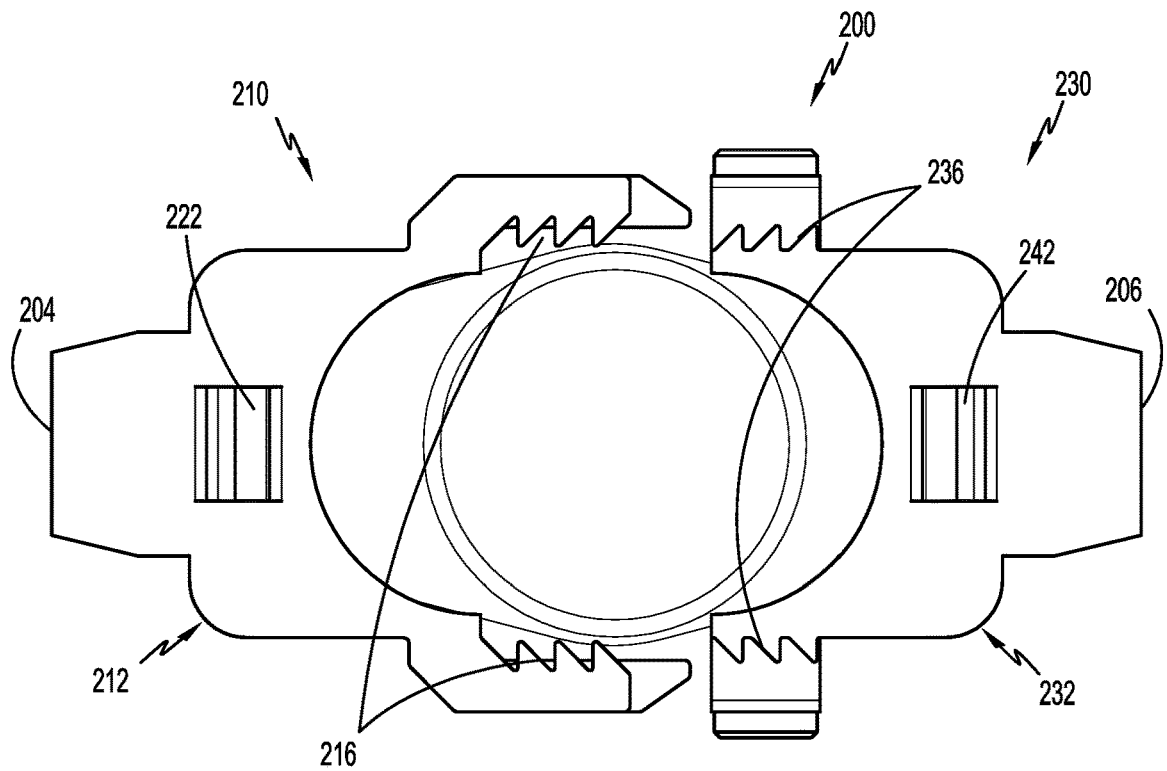
FIG. 8 is a top view of the retention mechanism as shown in FIG. 7.
Figure 9:
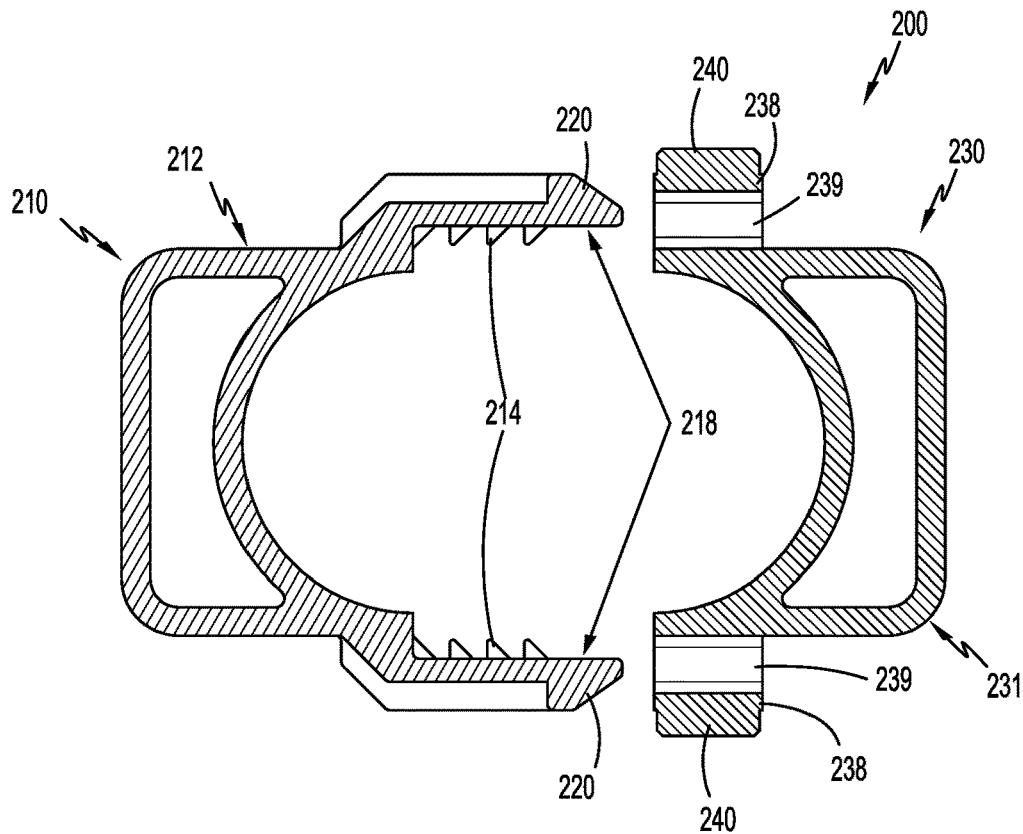
FIG. 9 is a top, cross-sectional view of the retention mechanism taken along section line 9-9 in FIG. 7.

FIGS. 7-9 illustrate the retention mechanism 200 with the first locking member 210 in alignment with the second locking member 230. More particularly, the first and second sets of opposed inwardly facing teeth 214, 216 of the first locking member 210 align with the opposed outwardly facing teeth 234, 236 of the second locking member 230 and the locking snaps 218 of the first locking member 210 align with the recess 239 of the support portion 238 of the second locking member 230.

Figure 10:
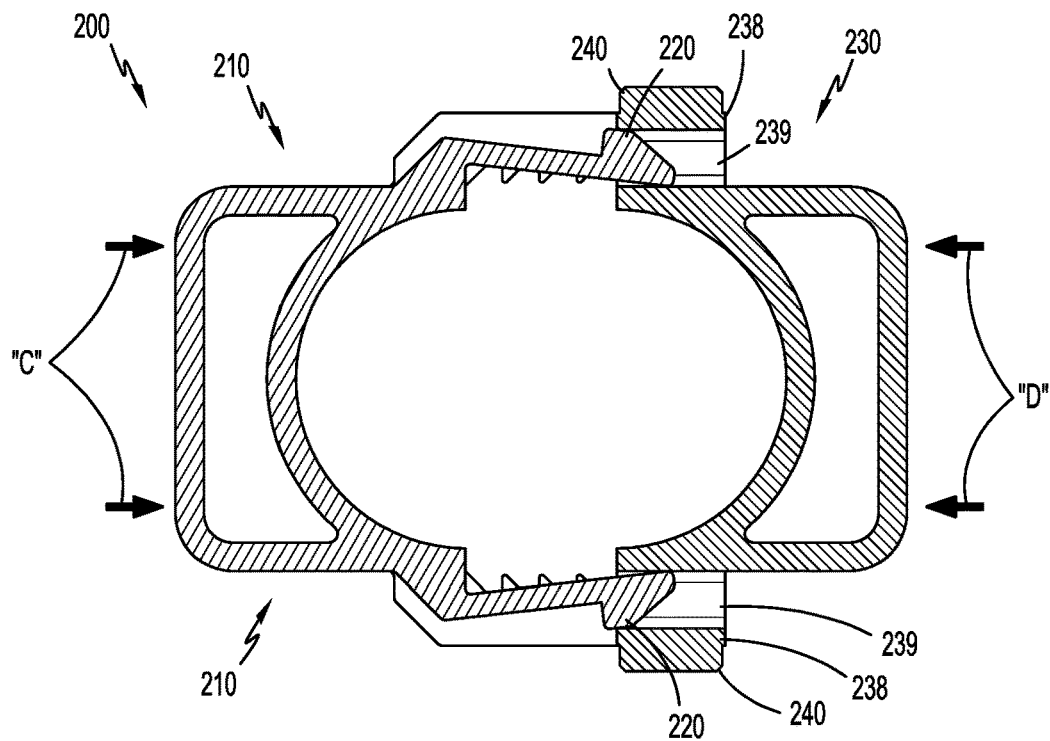
FIG. 10 is the top, cross-sectional view of the retention mechanism shown in FIG. 9, with the first and second locking members in a partially engaged condition.

FIG. 10 illustrates the retention mechanism 200 as the first and second locking members 210, 230 are moved relative to each other, as indicated by arrows "C" and "D", to cause the snap locks 218 of the first locking member 210 to be received within the recesses 239 of the locking portions 238 of the second locking member 230. The first and second locking members 210, 230 are approximated relative to each other until the locking tabs 220 of the snap locks 218 are received entirely through the recesses 239 in the locking portion 238 of the second locking member 230. In this manner, the locking tabs 220 of the snap locks 218 of the first locking member 210 engage the locking portion 238 of the second locking member 210 to secure the first and second locking members 210, 230 relative to each other.

Figure 11:
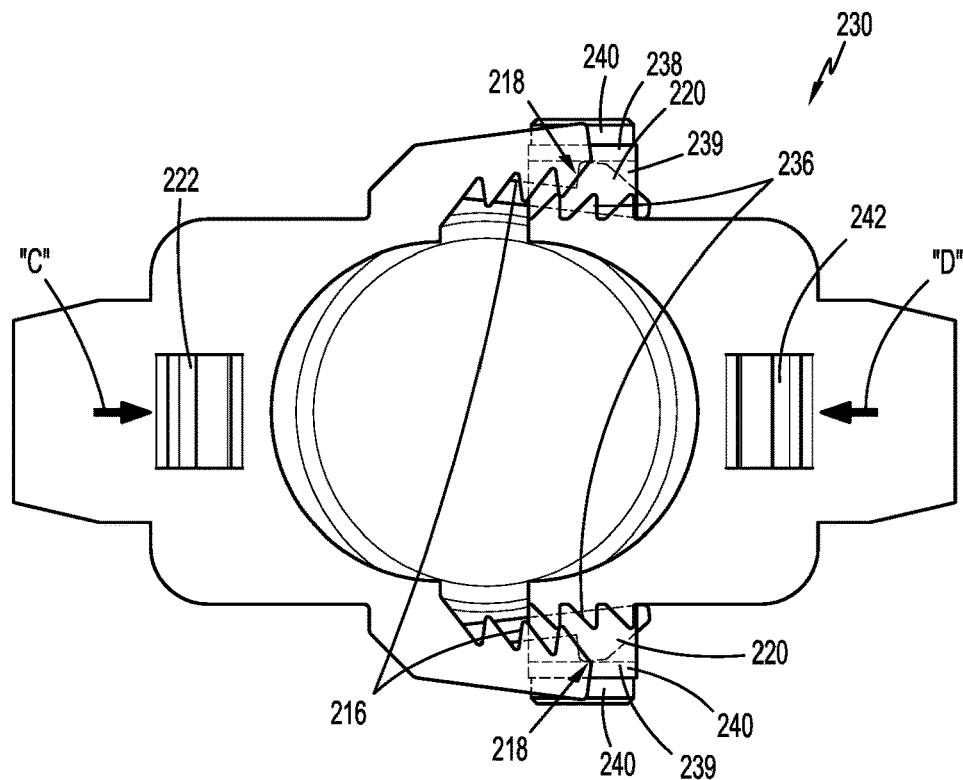
FIG. 11 is a top view of the retention mechanism as shown in FIG. 10.

FIG. 11 illustrates the engagement of the second sets of opposed, inwardly facing teeth 216 of the first locking member 210 with the second set of opposed, outwardly facing teeth 236 of the second locking member 230 as the locking tabs 220 of the snap locks 218 of the first locking member 210 are received through the recesses 239 in the support portion 238 of the second locking member 230. The first and second sets of opposed, inwardly and outwardly facing teeth 214, 216, 234, 236, of the first and second locking members 210, 230, respectively, are configured to ratchet against each other as the first and second locking members 210, 230 are approximated relative to each other to permit one way movement between the first and second locking members 210, 230.

Figure 12:
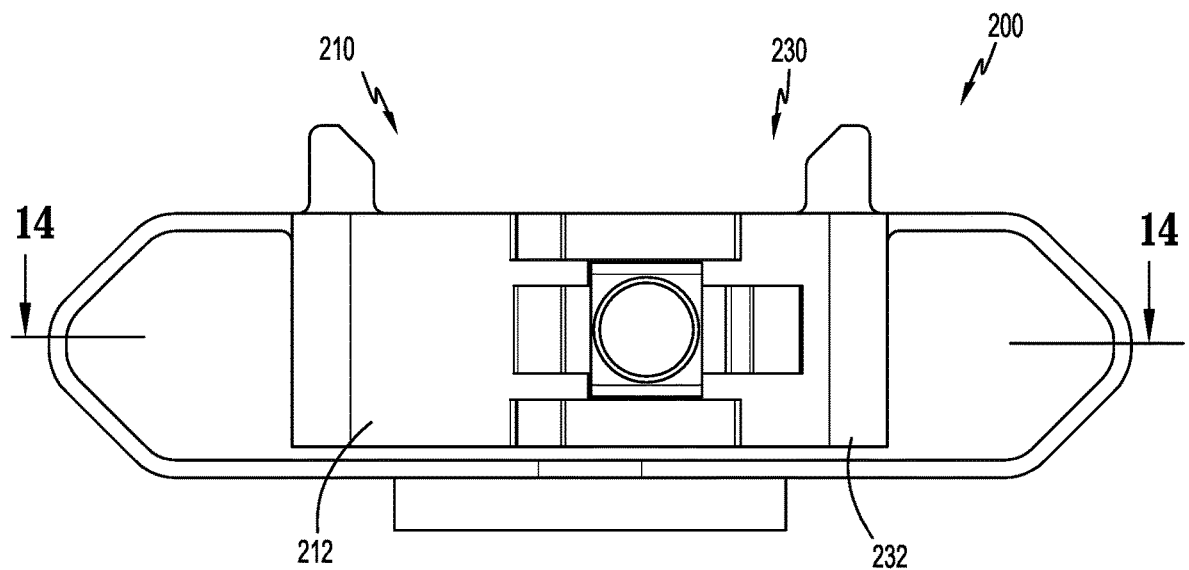
FIG. 12 is a side view of the retention mechanism shown in FIGS. 1-11, in a locked condition.
Figure 13:
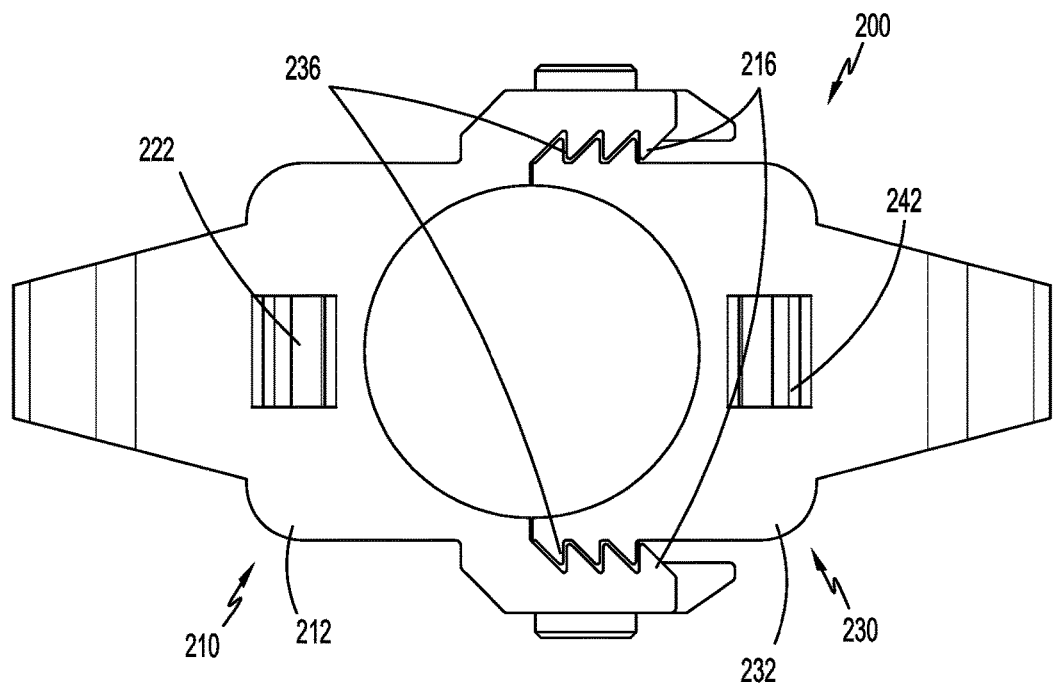
FIG. 13 is a top view of the retention mechanism as shown in FIG. 12.
Figure 14:
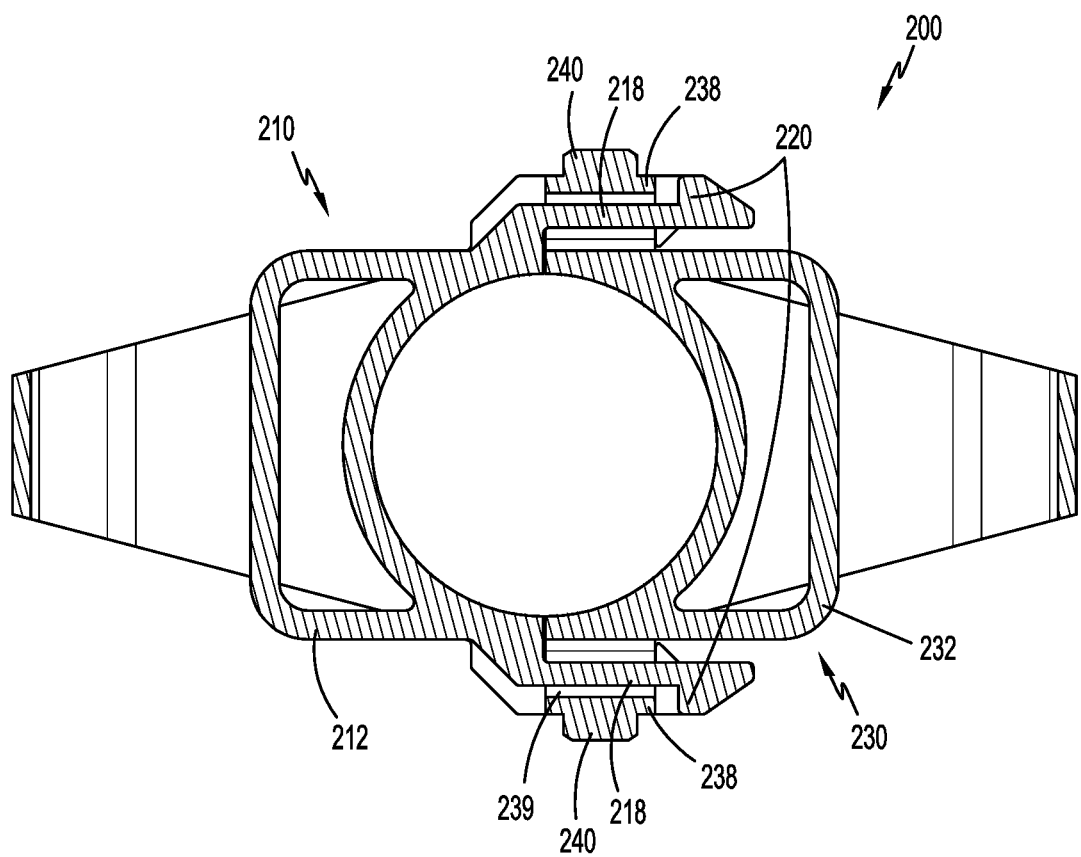
FIG. 14 is a top cross-sectional view of the retention mechanism taken along section line 14-14 in FIG. 12.

FIGS. 12-14 illustrate the retention mechanism 200 in a locked condition. In the locked condition, the first and second sets of opposed inwardly and outwardly facing teeth 214, 216, 234, 236 are fully engaged with one another.

Figure 16:
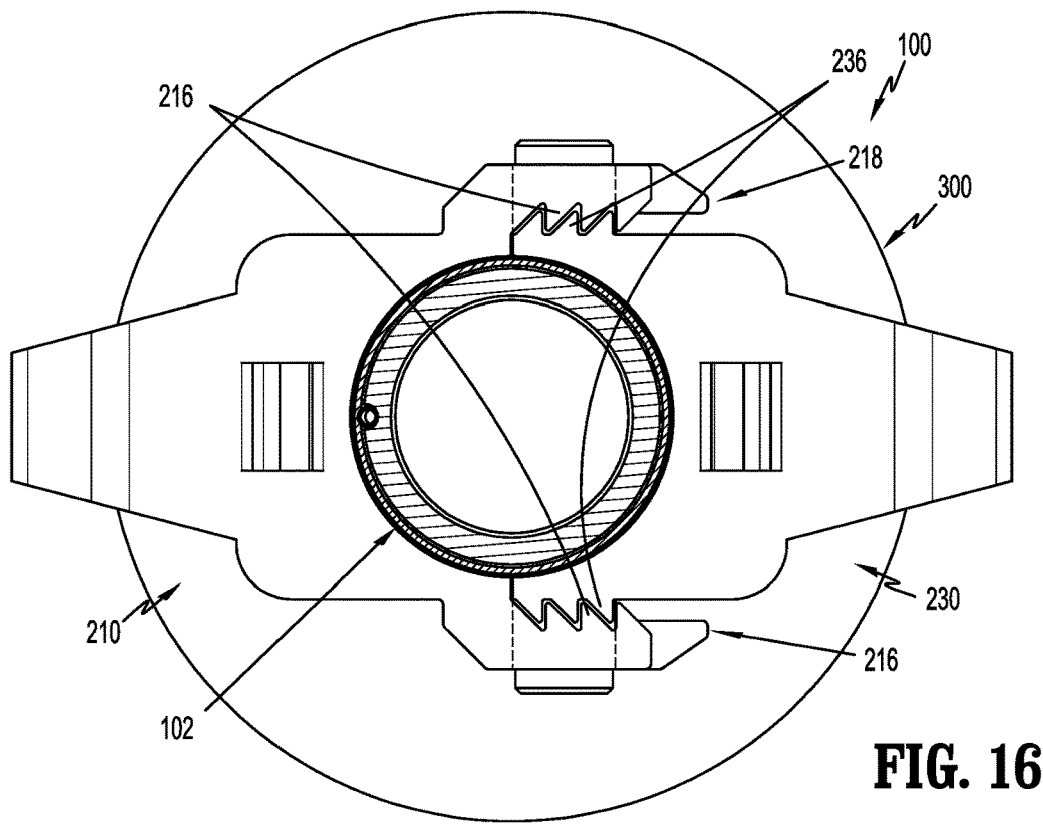
FIG. 16 is a top cross-sectional view of the access assembly taken along section line 16-16 of FIG. 15.

FIGS. 15 and 16 illustrate the retention mechanism 200 disposed about the cannula 102 of the access assembly 100 and in the locked condition. The distal end 102a of the cannula 102 is received within an incision "I" in tissue "T" of a patient with the anchor mechanism 120 of the access assembly 100 disposed within a body cavity "C" of the patient. A foam block 300 is received about the cannula 102 and is disposed between the retention mechanism 200 and the tissue "T" of the patient. In certain aspects of the disclosure, the foam block is permanently glued to or otherwise affixed to the retention mechanism 200.

When the retention mechanism 200 is secured to the access assembly 100 in the locked condition, the retention mechanism 200 is longitudinally fixed relative to the cannula 102. To permit longitudinal movement of the retention mechanism 200 relative to the cannula 102 of the access assembly 100 to secure the access assembly 100 to the tissue "T", the second locking member 230 is moved relative to the first locking member 210 to move the first and second set of opposed, outwardly facing teeth 234, 236 of the second locking member 230 out of engagement with the first and second sets of opposed, inwardly facing teeth 214, 216 of the first locking member 210, as indicated by arrows "E" and "F" in FIG. 17, to an unlocked condition (FIG. 17).

Figure 17:
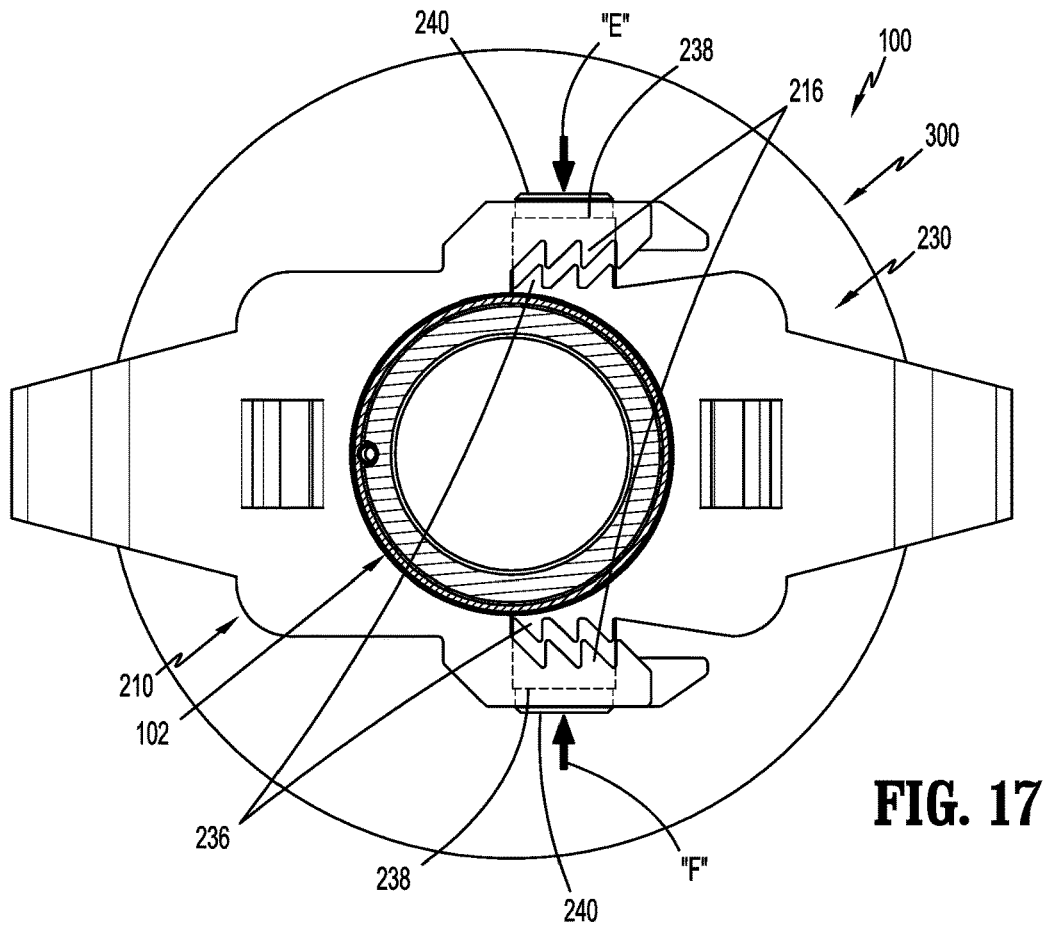
FIG. 17 is the top cross-sectional view of the access assembly shown in FIG. 16, with the first and second locking members of the retention mechanism in an unlocked condition.
Figure 18:
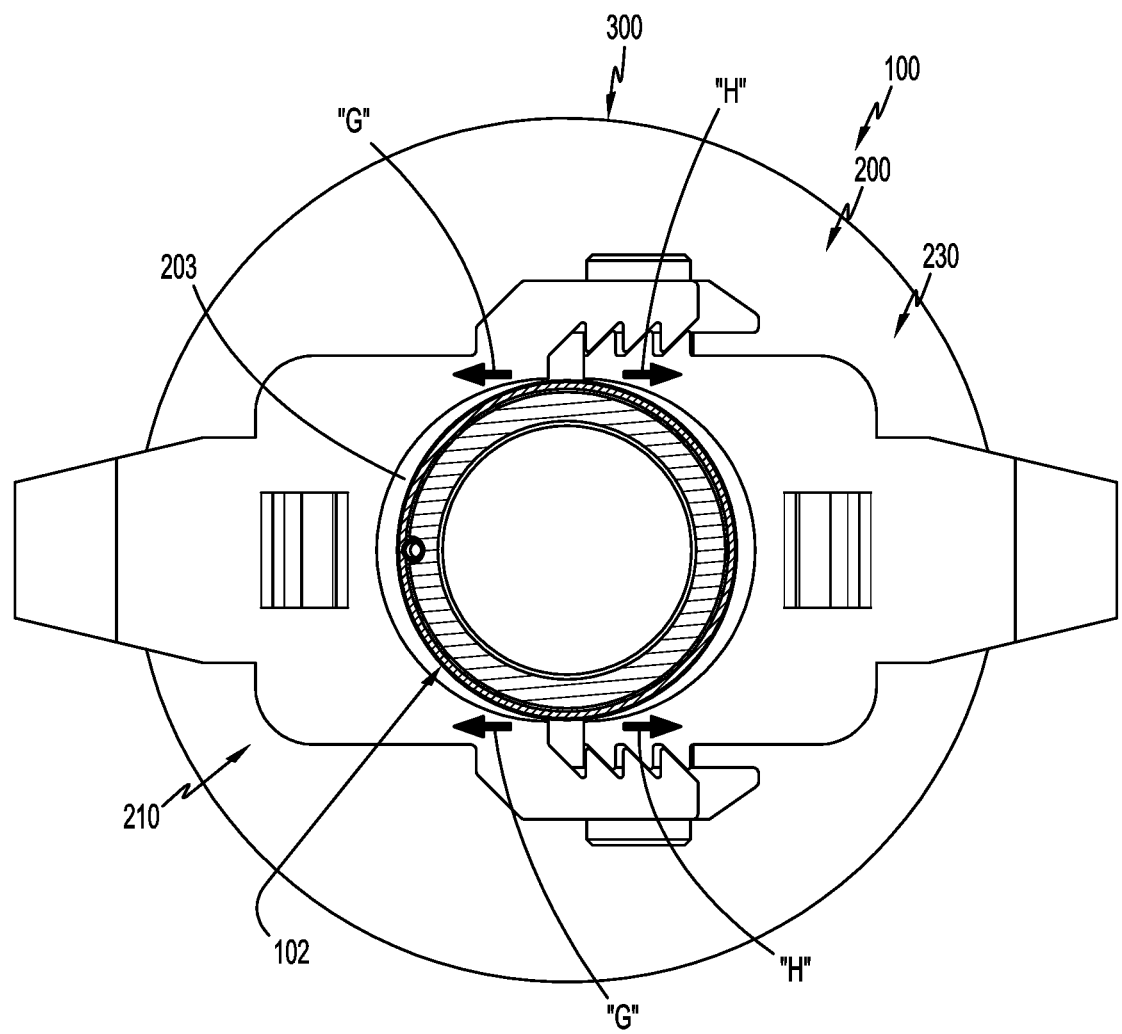
FIG. 18 is the top cross-sectional view of the access assembly shown in FIG. 16, with the first and second locking members of the retention mechanism in a partially locked condition.

FIG. 17 illustrates the first and second locking members 210, 230 of the retention mechanism 200 in the unlocked condition. In the unlocked condition, the first and second locking member 210, 230 are configured to move away from each other, as indicated by arrows "G" and "H" in FIG. 18, to a partially locked condition (FIG. 18). The button members 240 on the locking portions 238 of the second locking member 230 facilitates engagement of the second locking member 230 by a user (not shown) and movement of the first and second sets of opposed, inwardly facing teeth 234, 236 of the second locking member 230 away from the first and second sets of opposed outwardly facing teeth 214, 216 of the first locking member 210.

Figure 19:
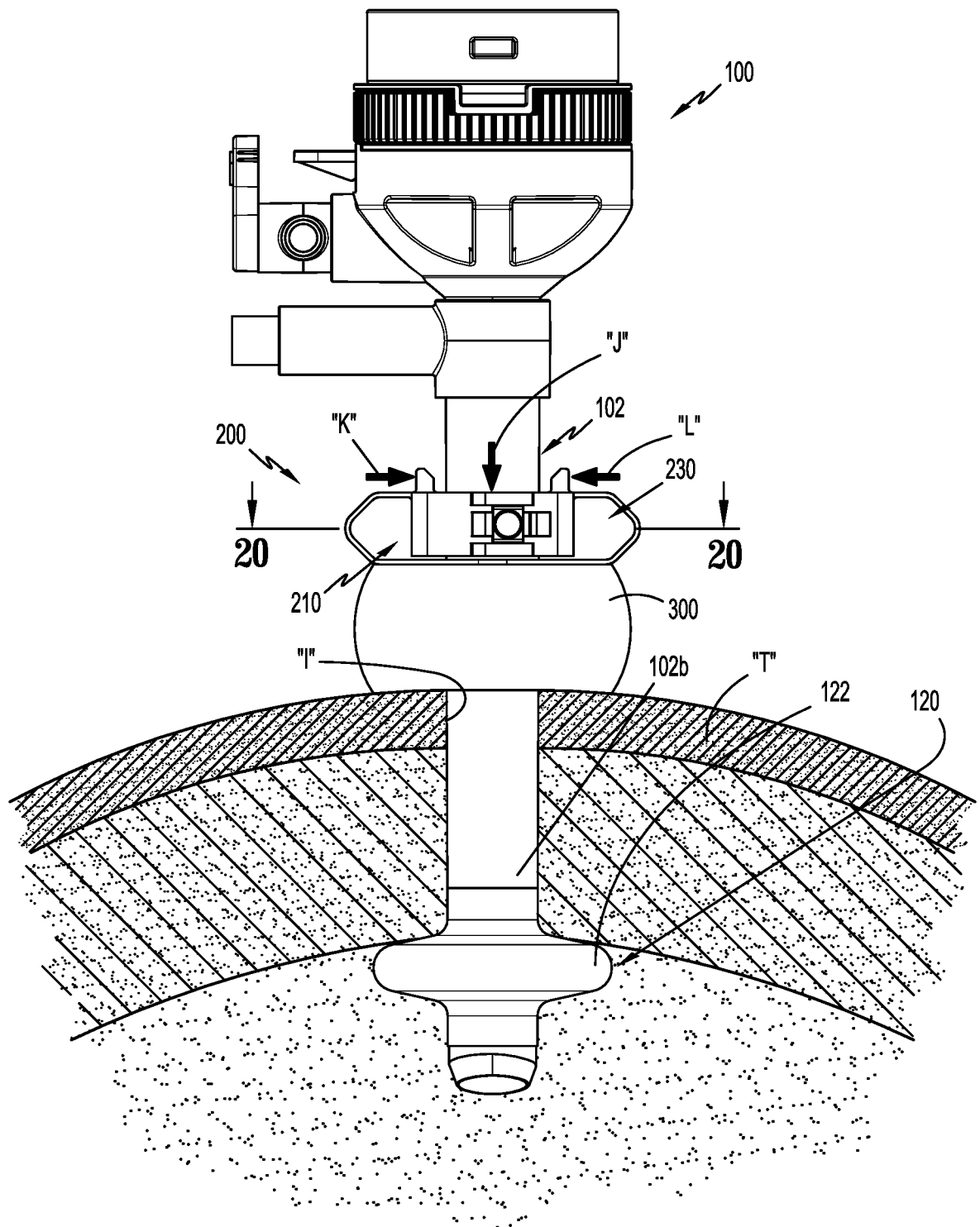
FIG. 19 is a side view of the access assembly shown in FIG. 16, with the first and second locking members of the retention mechanism in the locked condition.

FIGS. 18 and 19 illustrate the first and second locking members 210, 230 of the retention mechanism 200 in the partially locked condition. In the partially locked condition, the retention mechanism 200 is movable along the cannula 102 of the access assembly 100. In this manner, the retention mechanism 200 is movable toward the anchor mechanism 120, as indicated arrow "J" in FIG. 20, to compress the foam block 300 (FIG. 20) and sandwich the tissue "T" of the patient between the foam block 300 and the anchor mechanism 120 to secure the access assembly 100 relative to the tissue "T".

Figure 20:
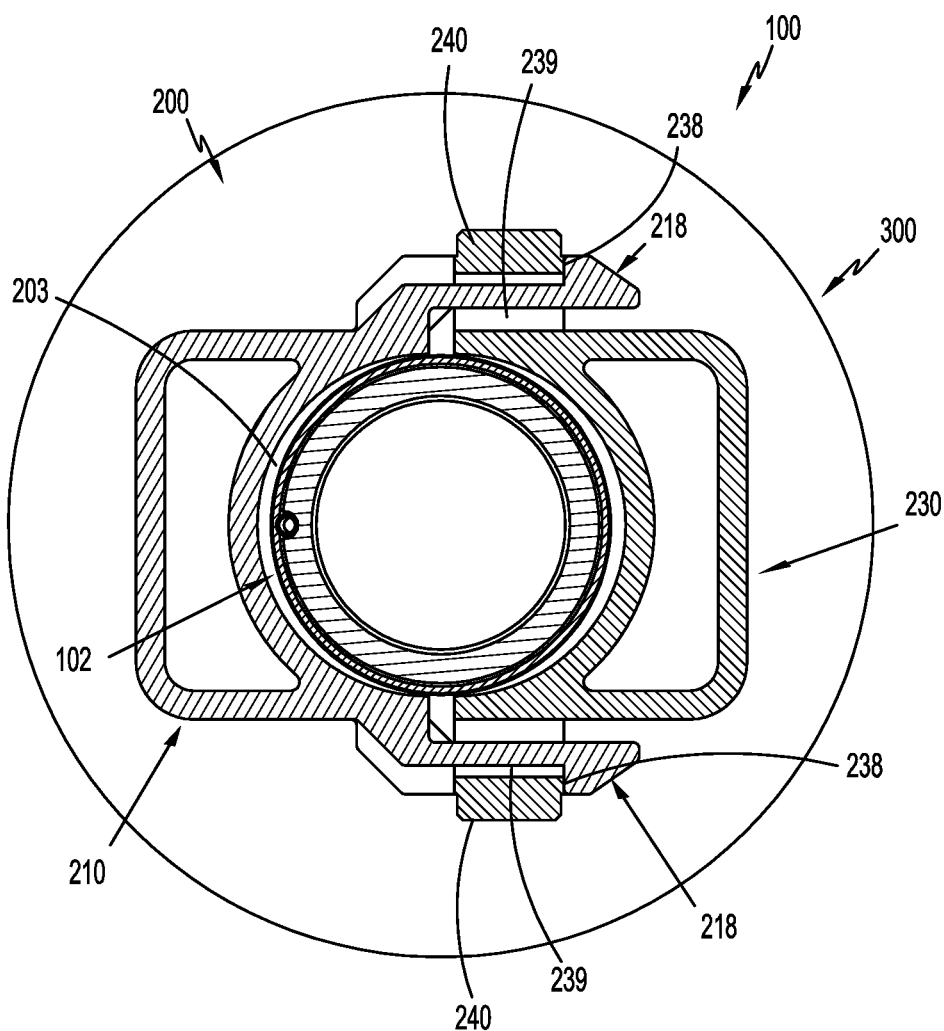
FIG. 20 is a cross-sectional top view of the access assembly shown in FIG. 19 taken along section line 20-20 in FIG. 19 with the retention mechanism is the partially locked condition.

FIG. 20 illustrates the retention mechanism 200 in the locked condition securing the access assembly 100 to the tissue "T". Following inflation of the balloon anchor 122 of the anchor mechanism 120, the retention mechanism 200 is slid distally along the cannula 102 to squeeze or sandwich the tissue "T" between the anchor mechanism 120 and the foam block 300. In this manner, the access assembly 100 is secured to the tissue "T" and the access assembly 100 is inhibited from longitudinal movement relative to the tissue "T" throughout insertion, withdrawal, and/or manipulation of a surgical instrument "I" through the access assembly 100.

As described above, the retention mechanism 200 is moved to the locked condition by approximating the first locking member 210 and the second locking members 230 relative to each other, as indicated by arrows "K" and "L", to frictionally engaged the retention mechanism 200 with the cannula 102 of the access assembly 100. The engagement members 222, 242 of the respective first and second locking members 210, 230 facilitate approximation of the first and second locking members 210, 230.

When the retention mechanism 200 is in the folded condition, the first and second extensions 204, 206 of the planar base 202 may be used as suture stays to receive sutures (not shown) to further secure the access assembly 100 during a surgical procedure.

Following a surgical procedure, the balloon anchor 122 of the anchor mechanism 120 may be deflated to permit withdrawal of the cannula 102 of the access assembly 100 from the tissue "T", with the retention mechanism 200 remaining secured to the cannula 102 of the access assembly 100. Prior to deflating the balloon anchor 122 of the anchor mechanism 120, the retention mechanism 200 may be moved to the partially locked condition (FIG. 18), as described above, to permit longitudinal movement of the retention mechanism 200 away from the anchor mechanism 120 and to permit expansion and/or movement of the foam block 300.

Persons skilled in the art will understand that the devices and methods specifically described herein and illustrated in the accompanying drawings are non-limiting exemplary devices. It is envisioned that the elements and features illustrated or described in connection with the exemplary devices may be combined with the elements and features of another without departing from the scope of the disclosure. As well, one skilled in the art will appreciate further features and advantages of the disclosure based on the above-described devices. Accordingly, the disclosure is not to be limited by what has been particularly shown and described, except as indicated by the appended claims.

What is claimed is:

1. A retention mechanism for a surgical access assembly, the retention mechanism comprising:
    a planar base having a first extension extending from a first side of the planar base and a second extension extending from a second side of the planar base, the planar base defining an opening, the first extension and the second extension each including a free end, the first extension, the second extension, and the planar base being substantially coplanar in an unlocked condition;
    a first locking member disposed on the free end of the first extension, the first locking member including a U-shaped body having a first free end and a second free end and a first set of opposed, inwardly facing teeth on each of the first free end and the second free end; and
    a second locking member disposed on the free end of the second extension, the second locking member including a U-shaped body having a third free end and a fourth free end and a first set of opposed, outwardly facing teeth on each of the third free end and the fourth free end configured to engage the first set of opposed, inwardly facing teeth when the retention mechanism is in a locked condition, wherein the first set of opposed, inwardly facing teeth and the first set of opposed, outwardly facing teeth are configured to be spaced apart from each other when the retention mechanism is in the unlocked condition.

2. The retention mechanism according to claim 1, wherein the first locking member includes a snap member disposed adjacent the first set of opposed, inwardly facing teeth and the second locking member includes a locking portion defining a recess for receiving the snap member of the first locking member.

3. The retention mechanism according to claim 2, wherein receipt of the snap member through the recess of the locking portion secures the first locking member and the second locking member relative to each other.

4. The retention mechanism according to claim 1, wherein the first locking member includes a second set of opposed, inwardly facing teeth and the second locking member includes a second set of opposed, outwardly facing teeth releasably engageable with the second set of opposed, inwardly facing teeth of the first locking member.

5. The retention mechanism according to claim 4, wherein the first locking member includes a snap member disposed between each of the first set of opposed, inwardly facing teeth and the second set of opposed, inwardly facing teeth, and the second locking member includes a locking portion defining a recess disposed between each of the first set of opposed, outwardly facing teeth and the second set of opposed, outwardly facing teeth of the second locking member.

6. The retention mechanism according to claim 5, wherein the snap members are configured to be received within the recess of the locking portions to secure the first locking member relative to the second locking member.

7. The retention mechanism according to claim 6, wherein receipt of the snap members within the recess of the locking portions secures the first locking member and the second locking member relative to each other.

8. The retention mechanism according to claim 1, wherein the second locking member includes button members for facilitating movement of the first set of opposed, outwardly facing teeth relative to the first set of opposed, inwardly facing teeth.

9. The retention mechanism according to claim 1, wherein each of the first extension and the second extension includes a narrow portion to permit folding of the respective first extension and second extension relative to the planar base.

10. The retention mechanism according to claim 1, wherein the first extension and the second extension are configured to receive sutures.

11. A surgical access assembly comprising:
a cannula having a distal portion and a length;
an anchor mechanism disposed on the distal portion of the cannula; and
a retention mechanism receivable about the length of the cannula, the retention mechanism including:
a planar base having a first extension and a second extension and defining an opening, each of the first extension and the second extension including a free end, the first extension being substantially coplanar with the second extension in a locked condition, the first extension and the second extension being laterally spaced from the planar base in the locked condition;
a first locking member disposed on the free end of the first extension, the first locking member including a U-shaped body having a first free end and a second free end and a first set of opposed, inwardly facing teeth on each of the first free end and the second free end; and
a second locking member disposed on the free end of the second extension, the second locking member including a U-shaped body having a third free end and a fourth free end and a first set of opposed, outwardly facing teeth on each of the third free end and fourth free end configured to engage the first set of opposed, inwardly facing teeth when the retention mechanism is in the locked condition and to be spaced apart from the first set of opposed, inwardly facing teeth when the retention mechanism is in an unlocked condition.

12. The surgical access assembly according to claim 11, wherein the first locking member includes a snap member disposed adjacent the first set of opposed, inwardly facing teeth and the second locking member includes a locking portion defining a recess for receiving the snap member of the first locking member.

13. The surgical access assembly according to claim 12, wherein receipt of the snap member through the recess of the locking portion secures the first locking member and the second locking member relative to each other.

14. The surgical access assembly according to claim 11, wherein the first locking member includes a second set of opposed, inwardly facing teeth and the second locking member includes a second set of opposed, outwardly facing teeth releasably engageable with the second set of opposed, inwardly facing teeth of the first locking member.

15. The surgical access assembly according to claim 14, wherein the first locking member includes a snap member disposed between each of the first set of opposed, inwardly facing teeth and the second set of opposed, inwardly facing teeth, and the second locking member includes a locking portion defining a recess disposed between each of the first set of opposed, outwardly facing teeth and the second set of opposed, outwardly facing teeth of the second locking member.

16. The surgical access assembly according to claim 15, wherein the snap members are configured to be received within the recess of the locking portions to secure the first locking member relative to the second locking member.

17. The surgical access assembly according to claim 16, wherein receipt of the snap members within the recess of the locking portions secures the first locking member and the second locking member relative to each other.

18. The surgical access assembly according to claim 11, wherein the second locking member includes button members for facilitating movement of the first set of opposed, outwardly facing teeth relative to the first set of opposed, inwardly facing teeth.

19. The surgical access assembly according to claim 11, wherein the anchor mechanism includes an inflatable balloon.

20. The surgical access assembly according to claim 11, further including a foam block positionable about the cannula between the anchor mechanism and the retention mechanism.

\* \* \* \* \*